US012064512B2

(12) United States Patent
Franz et al.

(10) Patent No.: US 12,064,512 B2
(45) Date of Patent: *Aug. 20, 2024

(54) SILYL LIPIDS SUITABLE FOR ENHANCED DELIVERY OF ANTI-VIRAL THERAPEUTICS

(71) Applicant: The Regents of the University of California, Oakland, CA (US)

(72) Inventors: Annaliese Franz, Davis, CA (US); Angel Cobo, Davis, CA (US); Leah Thompson, Davis, CA (US); David Coppage, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,011

(22) Filed: May 10, 2023

(65) Prior Publication Data
US 2023/0301913 A1 Sep. 28, 2023

Related U.S. Application Data

(63) Continuation of application No. 18/159,010, filed on Jan. 24, 2023.

(60) Provisional application No. 63/323,388, filed on Mar. 24, 2022.

(51) Int. Cl.
*A61K 9/127* (2006.01)
*A61K 31/7105* (2006.01)

(52) U.S. Cl.
CPC .......... *A61K 9/127* (2013.01); *A61K 31/7105* (2013.01)

(58) Field of Classification Search
None
See application file for complete search history.

(56) References Cited

FOREIGN PATENT DOCUMENTS

| | | |
|---|---|---|
| CN | 105664785 A | 6/2016 |
| DE | 4437886 A1 | 7/1996 |
| EP | 0691327 B1 | 7/1999 |
| EP | 2700645 A1 | 2/2014 |
| JP | H10147587 A | 6/1998 |
| JP | 5400003 B2 | 1/2014 |
| KR | 20120063331 A | 6/2012 |
| WO | 1997/026870 A1 | 7/1997 |
| WO | 2005/078482 A1 | 8/2005 |
| WO | 2008/011561 A2 | 1/2008 |
| WO | 2009/051580 A1 | 4/2009 |
| WO | 2012/078457 A1 | 6/2012 |

OTHER PUBLICATIONS

International Search Report and Written Opinion for international application PCT/US2023/011468, corresponding to this U.S. application, mailed May 12, 2023, 9 pages.
Aso Fumihiro et al., Efficient Inhibition of Re-blocking During the Deblocking of Blocked Isocyanates, Chemistry Select, Sep. 16, 2020, vol. 5, No. 35, 11063-11066.
Blakney, et al. "Inside out: optimization of lipid nanoparticle formulations for exterior complexation and in vivo delivery of saRNA." Gene therapy 26, No. 9 (2019): 363-372.
Fletcher, et al. "In vivo studies of dialkynoyl analogues of DOTAP demonstrate improved gene transfer efficiency of cationic liposomes in mouse lung." Journal of medicinal chemistry 49, No. 1 (2006): 349-357.
Fraenkel, et al. "Restricted stereochemistry of solvation of allylic lithium compounds: Structural and dynamic consequences." Journal of the American Chemical Society 121, No. 2 (1999): 432-443.
Hayashi, et al. "Chemical synthesis of dual labeled proteins via differently protected alkynes enables intramolecular FRET analysis." Chemical Communications 53, No. 43 (2017): 5918-5921., Database Calpus (online) Chemical Abstracts, Database accession No. 1703.
Hayashi, et al. Supporting Information "Chemical synthesis of dual labeled proteins via differently protected alkynes enables intramolecular FRET analysis." Chemical Communications 53, No. 43 May 10, 2017, pp. S1-D25.
Jaeger, et al. "Regioselectivity Control in Diels—Alder Reactions of Surfactant 1, 3-Dienes with Surfactant Dienophiles." Journal of the American Chemical Society 122, No. 12 (2000): 2749-2757.
Kajita, et al. "Design and synthesis of silicon-containing fatty acid amide derivatives as novel peroxisome proliferator-activated receptor (PPAR) agonists." Bioorganic & Medicinal Chemistry Letters 25, No. 16 (2015): 3350-3354.
Kamo, et al. "Silyl-protected propargyl glycine for multiple labeling of peptides by chemoselective silyl-deprotection." Tetrahedron Letters 73 (Apr. 17, 2021): 153093.
Liu et al., Enantioselective α-Silyl Amino Acid Synthesis by Reverse-Aza-Brook Rearrangement, Organic Letters, vol. 5, No. 24, Oct. 28, 2003, 4677-4679.
Mustafa Mohamed, et al. "Allylsilane-Modified Amino Acids from the Claisen Rearrangement." Helvetica chimica acta 85, No. 12 (2002): 4165-4181.
Nakamura, et al. "Design and synthesis of silicon-containing tubulin polymerization inhibitors: Replacement of the ethylene moiety of combretastatin A-4 with a silicon linker." Bioorganic & medicinal chemistry 21, No. 23 (2013): 7381-7391.

(Continued)

*Primary Examiner* — Celeste A Roney
(74) *Attorney, Agent, or Firm* — Kilpatrick Townsend & Stockton LLP

(57) ABSTRACT

This disclosure provides silyl lipid molecules in which one or more carbon-to-carbon double bonds in the lipophilic portion is substituted with a silicon atom. Guidance is provided by which the reader may make silyl lipid molecules from molecular building blocks, and then incorporate silyl lipid molecules into lipid nanoparticles (LNPs). The silyl LNPs can be used as carriers of pharmaceutical agents. Flexible steric and substitution patterns of silyl groups in the LNPs give the user a way to fine-tune physicochemical properties, achieving improved stability and clinical efficacy. This technology is useful for immunization or genetic therapy, such as the preparation and administration of RNA vaccines for protection against the virus that causes COVID-19.

18 Claims, 10 Drawing Sheets

(56) References Cited

OTHER PUBLICATIONS

Figure 1A:
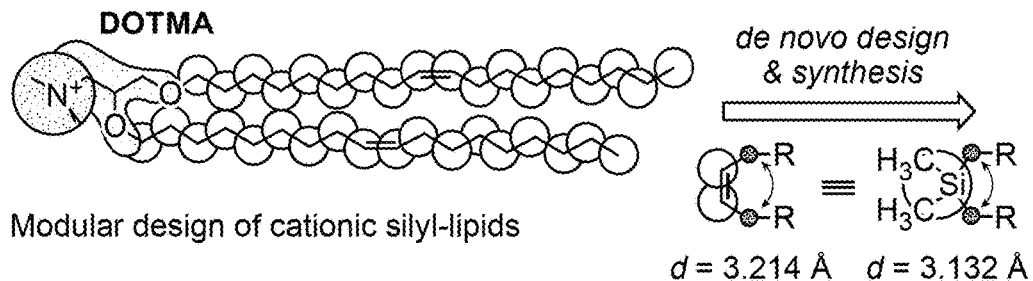
Figure 1B:
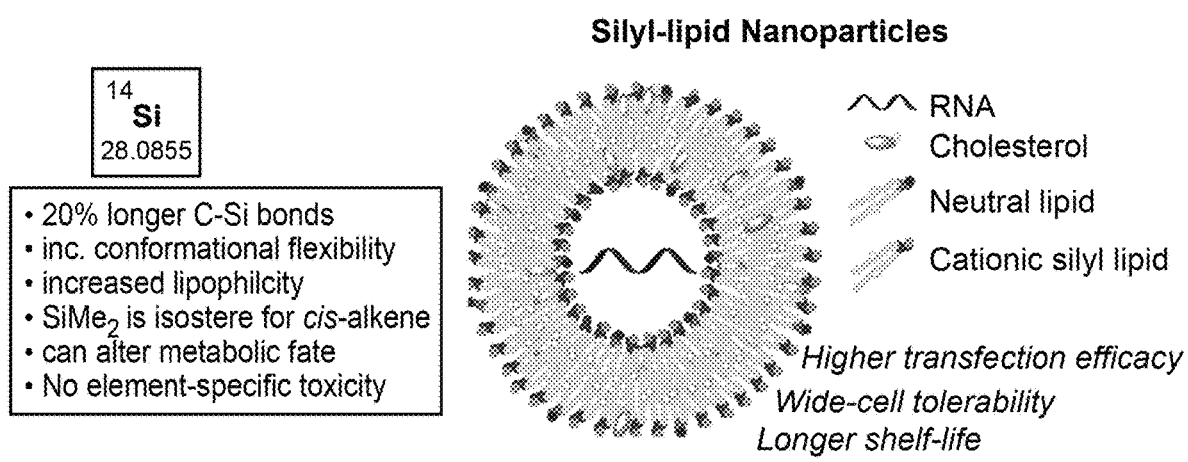

Nishimura, et al. "Rhodium-catalyzed enantioselective 1, 6-addition of arylboronic acids to enynamides: asymmetric synthesis of axially chiral allenylsilanes." Journal of the American Chemical Society 132, No. 37 (2010): 12865-12867.

Norihiko et al., Preparation of 2-Amino-1, 3-Propanediols and Their Use as Immunosuppressants, XP093042522, Database accession No. 1998:352139, Abstract.

Database Reaxys (online); Elsevier Reaxys Jun. 15, 2016, Li Rongqiang et al., A Polumerization of the Acryloxy-Containing Three Poly-Cationic Surface Active Agent and its Preparation method, XP093042261, Database accession No. Reaxys ID: 45205562.

Rodríguez, et al. "Palladium-Catalyzed Hydride Addition/C—H Bond Activation Cascade: Cycloisomerization of 1, 6-Diynes." Organic letters 20, No. 21 (2018): 6915-6919.

Kazuhiko Sakaguchi, et al. "Chirality transferring [3, 3] sigmatropic rearrangement of (1-acyloxy-2-alkenyl) trialkylsilane synthesis of optically active vinylsilane-containing α-amino acid." Chirality: The Pharmacological, Biological, and Chemical Consequences of Molecular Asymmetry 13, No. 7 (2001): 357-365.

Sasaki, et al. "Chirality transfer in Brook rearrangement-mediated SE2' solvolytic protonation and its use in estimation of the propensity for racemization of the α-lithiocarbanions of the substituents." Tetrahedron 69, No. 29 (2013): 5823-5828.

Showell, et al. "Chemistry challenges in lead optimization: silicon isosteres in drug discovery." Drug discovery today 8, No. 12 (2003): 551-556.

Wan et al., "Synthesis of β-Silyl α-Amino Acids via Visible-Light Mediated Hydrosilylation," Organic Letters Feb. 19, 2021, 23, 1406-1410.

Zhi, et al. "Transfection efficiency of cationic lipids with different hydrophobic domains in gene delivery." Bioconjugate chemistry 21, No. 4 (2010): 563-577.

DOPE $n_1 = 2, 4, 5$
$n_2 = 1, 3, 5, 6, 8$

Silyl-DOPE

DOPE-PEG $n_1 = 2, 4, 5$
$n_2 = 1, 3, 5, 6, 8$

Silyl-DOPE-PEG

Cholesterol

*wherein*

Cationic Silyl Lipid     FIG. 5A

Silyl-DOTAP  Silyl-DOTMA

Silyl-DOPE

Silyl-DOPE-PEG

*wherein:*

$n_1$ = 2, 4, 5, 7
$n_2$ = 0, 1, 3, 5, 7, 8, 9, 10
$R_1$ = H, Me, OEt, Et, tBu, iPr
$R_2$ = Me, Cy, Ph, $(CH_2)_3$Ph, Et, OEt, iPr, OTMS, OTES, $O(SiMe_2)$OTMS

All lipids above can also have the tail shown below:

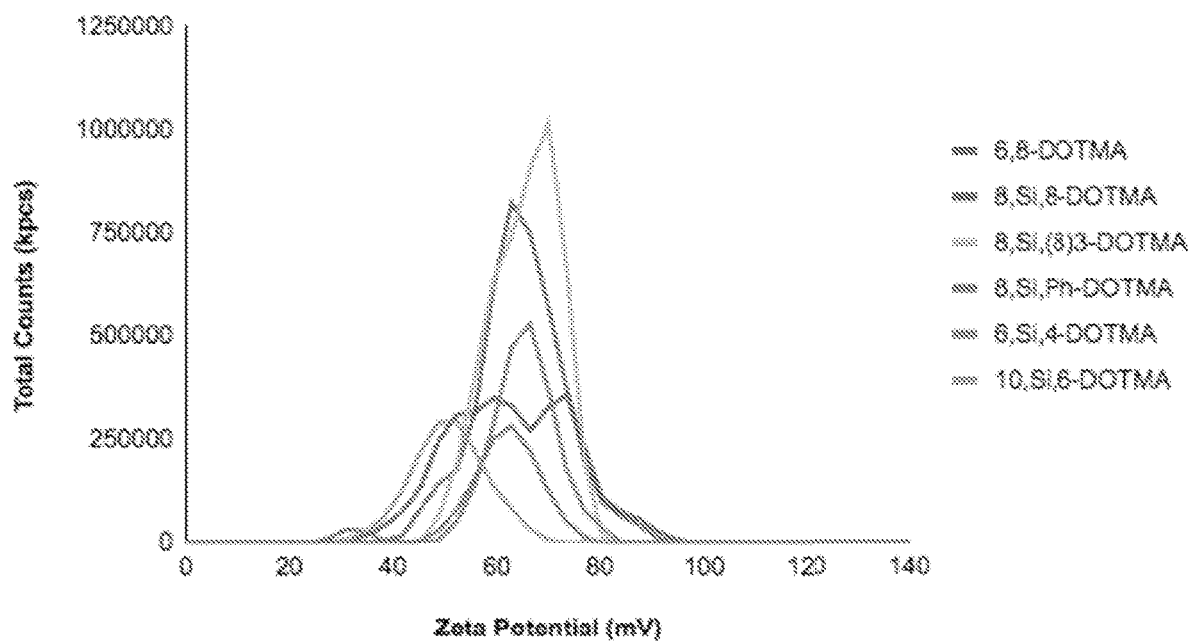

SILYL LIPIDS SUITABLE FOR ENHANCED DELIVERY OF ANTI-VIRAL THERAPEUTICS

RELATED APPLICATIONS

This application is a continuation of U.S. patent application Ser. No. 18/159,010, filed Jan. 24, 2023, which claims the priority benefit of U.S. provisional application 63/323,388, filed Mar. 24, 2022. The aforesaid priority applications are hereby incorporated herein by reference in their entireties for all purposes.

GOVERNMENT RIGHTS

This invention was made with government support under Grant No. 1R03EB033487-01 awarded by the National Institutes of Health. The U.S. Government has certain rights in the invention.

FIELD OF THE INVENTION

The technology disclosed and claimed below relates generally to the fields of lipid chemistry, lipid microparticles, genetic therapy, and immunopharmaceuticals. More specifically, it provides improvements in lipid nanoparticles with improved properties for use in vaccines.

BACKGROUND

COVID-19 is an ongoing global pandemic caused by a virus named as the severe acute respiratory syndrome coronavirus 2 (SARS-CoV-2). It was first identified from an outbreak in December 2019. Attempts to contain it at the initial site failed, allowing it to spread across the globe.

COVID-19 symptoms range from undetectable to deadly, but most commonly include fever, dry cough, loss of a sense of smell, and fatigue. Severe illness is more likely in elderly patients and those with certain underlying medical conditions. Infected persons are typically contagious for 10 days, and can spread the virus even if they do not develop symptoms. Mutations have produced many variants with different degrees of infectivity and virulence. As of January of 2023, COVID-19 has caused more than 1.1 million deaths in the U.S. and 6.7 million deaths worldwide, making it one of the deadliest virus-induced diseases in history.

Vaccines against SARS-CoV-2 are widely credited for reducing the severity and death caused by COVID-19. Some of the most rapidly developed and successful vaccines are based on recombinant RNA technology: either viral vectors or messenger RNA (mRNA), which both cause cells to express the spike protein presented on the surface of SARS-CoV-2. This stimulates the immune system to develop protective antibody and T-cells against the spike protein.

The delivery of mRNA is achieved by a co-formulation of the molecule into lipid nanoparticles which protect the RNA strands and help their absorption into the cells. Krammer F (October 2020), Nature. 586 (7830): 516-527; Kowalski PS et al. (April 2019) Molecular Therapy. 27 (4); Verbeke R et al, Nano Today. 28: 100766. Lipid nanoparticles for mRNA delivery has been reviewed by X. Hou et al. (December 2021), Nature Review Materials 6:1078-1094.

RNA vaccines for COVID-19 that are currently authorized for clinical use in the U.S. and Europe have been developed and distributed by Pfizer-BioNTech and by Moderna. They play central roles in the clinician's arsenal to decrease spread of COVID-19. Current RNA lipid vaccines must be stored at −20° C. or −80° C. Severe allergic reactions are rare. The COVID-19 RNA vaccine from CureVac failed in clinical trials (Press release, Jun. 30, 2021). Lipid technologies incorporated into the Moderna and BioNTech vaccines are described in U.S. Pat. Nos. 10,266,485 and 10,576,146 respectively.

SUMMARY

This disclosure provides silyl lipids in which one or more carbon-to-carbon double bonds in the lipophilic portion is substituted with a silicon atom. Guidance is provided by which the reader may make silyl lipids from molecular building blocks, and then incorporate silyl lipids into lipid nanoparticles (LNPs). The silyl LNPs can be formulated as carriers of pharmaceutical agents. Flexible steric and substitution patterns of silyl groups in the LNPs allow the user to fine-tune physicochemical properties, achieving improved stability and clinical efficacy. This technology is useful for immunization or genetic therapy, such as the preparation and administration of RNA vaccines for protection against the virus that causes COVID-19.

Included as part of this disclosure are silyl lipids, and nanoparticles containing such silyl lipids. The silyl lipids described in more detail in the sections that follow include lipids that have the structure shown in Formula I:

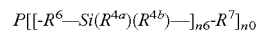

Formula I

P is a polar headgroup containing 2 to 25 carbon atoms, 2 to 8 oxygen atoms, and at least one nitrogen atom that is ionizable or positively charged; $R^{4a}$ and $R^{4b}$ are independently selected from methyl and a linear alkyl group of at least 4 carbon atoms. $R^6$ and $R^7$ are hydrocarbons of 2 to 20, 2 to 15, or 2 to 12 carbon atoms: usually linear, but optionally branched, and optionally having a different end group $R^8$, which may be a substituted or unsubstituted hydrocarbon. The $R^7$ and $R^8$ for each of the tails may be the same or different. n6 (the number of silicon atoms per lipid tail) is between 1 and 4; and n0 (the number of lipid tails per lipid molecule) is between 1 and 6.

$R^{4a}$ and $R^{4b}$ may both be methyl. The lipids may have branched fatty acid tails wherein at least one of $R^{4a}$ and $R^{4b}$ is a linear alkyl group of at least 4 carbon atoms. The silyl lipids may contain two $[-(CH_2)_{n2}-Si(R^{4a})(R^{4b})-(CH_2)_{n3}-CH_3]$ groups which are identical or non-identical. The polar headgroup of the silyl lipids may contains or be conjugated to polyethylene glycol.

The silyl lipids may have the structure shown in Formula III:

[Formula III]

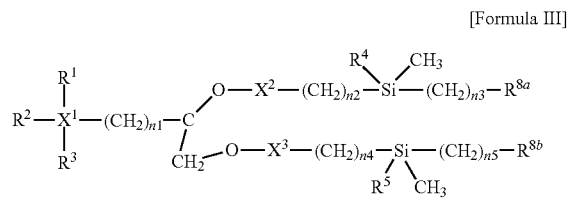

$R^1$, $R^2$, and $R^3$ are independently H, —$CH_3$, or a substituted or unsubstituted hydrocarbon containing two to ten carbon atoms, $X^1$ is nitrogen or —($OPO_3$)—, $X^2$ and $X^3$ are independently methylene or carbonyl or together are a quaternary carbon; $R^4$ and $R^5$ are independently selected from methyl and a linear or non-linear (optionally substituted) hydrocarbon of 4 to 12 carbon atoms; n1=1 to 6; and n2, n3, n4 and n5 are independently 4 to 12.

$X^1$ may be nitrogen, or it may be phosphate. $R^1$, $R^2$, and $R^3$ are all —$CH_3$. In one example. $R^1$ and $R^2$ are both —$CH_3$ and $R^3$ is a substituted hydrocarbon containing two to ten carbon atoms. In another example, $R^1$ is H, $R^2$ is —$CH_3$ and $R^3$ is a substituted or unsubstituted, optionally linear hydrocarbon containing two to ten carbon atoms.

Referring to Formula III, any one or more of the following features may be included in any combination: n1 is 1; $X^2$ and $X^3$ are both methylene or both carbonyl; n2 and n4 are both 7; n3 and n5 are both 7; $R^4$ and $R^5$ are both methyl; and/or $R^4$ and $R^5$ are both independently a linear hydrocarbon of 6 to 10 carbon atoms; $R^{8a}$ and $R^{8b}$ are each methyl or a saturated or unsaturated hydrocarbon of 2 to 10 or 2 to 6 carbons, such as —$CH_3$, cyclohexyl, or phenyl. Optionally, some of the silyl lipids in the preparation are PEGylated, whereby any one or more of $R^1$, $R^2$, and $R^3$ contain —O—[$CH_2$—$CH_2$—O—$]_{n9}$—$R^9$. The $R^9$ substituent may be —OH, —$OCH_3$, —$NH_2$, or a substituted hydrocarbon, and n9 is an integer of 10 or more.

A variant of Formula III incorporating a silicon substituted carbocycle, such as silicon substituted cyclobutane, cyclopentane, or cyclohexane. This is depicted in Formula IIIa, where n is 0 to 4, typically 1 or 2.

[Formula IIIa]

$$R^2-X^1-(CH_2)_{n1}-\underset{\underset{R^3}{|}}{\overset{\overset{R^1}{|}}{C}}\begin{matrix}-O-X^2-(CH_2)_{n2}-Si-(CH_2)_{n3}-R^{8a}\\ \\ CH_2-O-X^3-(CH_2)_{n4}-Si-(CH_2)_{n5}-R^{8b}\end{matrix}\begin{matrix}CH_2-(CH_2)_n-CH_2\\ \\ CH_2-(CH_2)_n-CH_2\end{matrix}$$

Nanoparticles made from the silyl lipids disclosed herein typically contain at least 2%, 5%, or 10% silyl lipids. In certain implementations of the technology, at least 25% of lipids in the nanoparticles are silyl lipids, and/or at least 50% of the silyl lipids in the nanoparticles are cationic and/or comprise a headgroup that is ionizable. The lipid nanoparticle may contain cationic lipids, ionizable lipids, and PEGylated lipids all together, any one, two, or all three of which may be silylated, or contain a proportion that is in silylated form. The lipid nanoparticle may also contain cholesterol.

The lipid nanoparticles may be solid nanoparticles comprising a lipid monolayer surrounding a drug payload. Alternatively, they may be liposomes enveloping a drug payload. The solid nanoparticles or liposomes may have an median diameter between 20 and 500 nm, or have other dimensions as put forth below.

The drug payload in the nanoparticles may comprise a nucleic acid for gene therapy or immunization of a subject in need thereof. By way of example, the drug payload comprises a messenger RNA (mRNA) or other nucleic acid that encodes a tumor antigen for eliciting an immunological response against a tumor in the subject being treated. Alternatively, the payload may include a protein component of a pathogen or a nucleic acid encoding such protein component, such as the spike protein of SARS-CoV-2 (the virus that causes COVID-19) or an immunogenic portion thereof.

This disclosure includes methods of gene therapy and methods of eliciting a specific immune response. A pharmaceutical product comprising a plurality of nanoparticles as put forth herein is administered to a subject in need thereof. The disclosure includes the use of the silyl lipids and nanoparticles as heretofore described for treating or preventing a disease or eliciting an immune response in a subject, or for preparation of a medicament for such purpose.

This disclosure also provides a method of improving a previous design or preparation of lipid nanoparticles. To do this, the user determines one or more lipids contained in the previous preparation that have one or more cis-unsaturated carbon-carbon bonds in one or more fatty acids in the lipid(s). They then design a silyl lipid in which one or more of the cis-unsaturated carbon-carbon bonds is substituted, for example, with [—$CH_2$—Si (($CH_3$)$_2$—$CH_2$—], or with [—$CH_2$—Si($R^x$)$_2$—$CH_2$—], wherein each $R^x$ is independently a hydrocarbon. The user then produces an improved preparation of lipid nanoparticles that contain the silyl lipid as well as or in place of one or more of the lipids contained in the previous preparation.

The silyl lipid may have one or more cis-unsaturated carbon-carbon bond that have been silylated. Examples include but are not limited to DOTMA, DOTAP, DOSPA, ePC, DLin-MC3-DMA, A2,iso-5-2DC18, OF-Deg-Lin, and DOPE.

Without intending to otherwise limit the practice of the technology put forth in this disclosure, an example is use of the technology to prepare an immunogenic composition formulated for administration to a subject for prevention or treatment of COVID-19. The composition includes a plurality of nanoparticles that contains a drug payload. Typically, at least 2%, 5%, 10%, or 20%, or 50% of lipids in the nanoparticles are silyl lipids having the structure shown in Formula I, II, III, or IIIa, and including any one or more of the features put forth below in any combination.

To elicit the immune response in the subject being treated, the drug payload includes one or more protein components of SARS-CoV-2 (the virus that causes COVID-19), optionally in combination with an immunological adjuvant, and/or one or more nucleic acids encoding such protein components. For example, the drug payload may include a messenger RNA (mRNA) encoding any one or more of the S (spike), E (envelope), M (membrane), and/or N (nucleocapsid) of the SARS-CoV-2 virus (including any naturally occurring or artificial variants thereof), or and immunogenic portions thereof in any combination.

The reference sequence for the severe acute respiratory syndrome coronavirus 2 isolate Wuhan-Hu-1 can be obtained from GenBank accession No. NC_045512 (Wu F et al., Nature 579 (7798): 265-269, 2020). The amino acid sequence of protein components of SARS-CoV-2 virus can be obtained from GenBank accession No. MT108784 (Thi Nhu Thao, T., Nature 582 (7813), 561-565, 2020). For example, silyl lipid nanoparticle vaccines according to this disclosure can be generated with a drug payload that comprises a nucleic acid or mRNA that encodes a protein that is at least 50%, 70%, 80%, 90%, or 95% identical to the spike protein sequence listed in GenBank accession No. MT 108784, deposited on 11 Feb. 2022, or any immunogenic portion thereof.

The silyl lipids and the lipid nanoparticle may have any of the features referred to above. In a particular formulation, the lipids in the nanoparticle include cationic lipids, ionizable lipids, and PEGylated lipids together in any effective amount and proportion, any one or more of which are silyl lipids. For example, the nanoparticle may contain any one or more of the following components in silylated form: DOTMA (1,2-di-O-octadecenyl-3-trimethylammonium-propane), DOTAP (N-(1-(2,3-dioleoyloxy)propyl)-N,N,N-trimethylammonium chloride), DOPE (2-dioleoyl-sn-glycero-3-phosphoethanolamine), and PEGylated DOPE.

This disclosure includes methods for inducing a specific immune response in a subject at risk of contracting COVID-19 by administering to the subject the nanoparticles referred to above. Other possible drug payloads and their use are put forward in Tables 1 and 2 below.

Aspects and embodiments of the technology are presented in the description, drawings, and claims that follow.

BRIEF DESCRIPTION OF THE DRAWINGS

FIGS. 1A and 1B show an example in which a silicon atom in the form of a silyldimethyl or silylcycloakyl group are incorporated into the target lipid DOTMA (1,2-di-O-octadecenyl-3-trimethylammonium-propane) in place of a carbon-carbon double bond. Lipid nanoparticles (LNPs) manufactured with silyl lipids have improved physicochemical and pharmaceutical properties compared with their non-silylated counterparts.

FIG. 2 is a scheme of chemical reagents and synthesis, whereby several families of molecular building blocks and precursors are used to produce silyl lipids with a silicon atom placed at a precise location in the lipid structure.

FIGS. 3A and 3B show lipids with unsaturated fatty acid tails that are currently used or proposed for use in LNPs. They can be converted to their silyl analogs and used to prepare improved LNPs in accordance with this disclosure.

FIG. 4 shows DOPE (2-dioleoyl-sn-glycero-3-phosphoethanolamine) in its standard form, and as a silyl lipid incorporating a single methylated silicon atom in the form of [$-Si(CH_2)_2$-] into each of the two lipid tails. Also shown are PEGylated forms of both DOPE and Silyl-DOPE, wherein the charged head group is conjugated to polyethylene glycol. Nanoparticles containing cationic lipids, ionizable lipids, and PEGylated lipids all together as part of the lipid content (at least one of which is in silylated form) have beneficial properties that improve preparation, stability, and therapeutic efficacy.

FIGS. 5A to 5C illustrate effects of lipid structure on properties of liposomes made from such lipids. There was a substantial effect on yield, particle diameter, and zeta potential.

FIG. 6 shows possible alternative lipophilic groups placed at or near the lipid tail of silyl lipids to instill nanoparticles made therefrom with beneficial properties.

FIGS. 7A to 7C illustrate how structure structural features such as tail length, positioning of the silicon group, and branching can affect properties of nanoparticles.

DETAILED DESCRIPTION

Before the making of the technology provided below, lipid nanoparticles (LNPs) for drug delivery have been designed by (1) modifying the procedure for forming nanoparticles using ionizable cationic lipids, and (2) modifying the chemistry of the hydrophobic head-group. There has been less emphasis on structural modifications of the lipid component, due to a general limitation in lipid pharmacophore options.

This disclosure provides new silyl-containing lipids that can be used to prepare improved LNPs with superior properties: better stability, powerful adjuvant potential, and enhanced delivery activity. The family of silyl-lipids provided in this disclosure can be fine-tuned to create new structures, varying the position of the silyl group, incorporating branched structures, and varying chain length.

Membrane fluidity is a contributing factor in transfection and the subsequent endosomal release of the drug payload after endocytosis. The presence of structural features such as a cis-unsaturation in the lipid tail helps prevent tight membrane packing. This promotes membrane fluidity, and positively influences transfection into cells. The dimethyl silyl or the silacycloalkane group has steric effects that can mimic a cis-alkene in bond distances and angles, potentially enhancing membrane fluidity. Moving the position of the silyl group and installing various substitutions on the silyl group, including aryl, alkyl, and cycloalkyl can also be used to fine-tune membrane fluidity and other properties of nanoparticles that contain them.

The silicon group can comprise two methyls or other R groups, or a silicon substituted cycloalkyl group such as silalyclobutyl, silacyclopentyl or silylcyclohexyl. Besides effects on membrane fluidity, replacing cis-alkene groups in non-saturated lipids with such silicon groups helps stabilize nanoparticles, rendering them less prone to oxidative damage.

Use of Silyl Lipids for Preparing LNPs

Liposomes such as nucleic acid complexed lipid nanoparticles (LNPs) have been successfully used in drug delivery and formulation of sensitive RNA-based therapeutics, including the recent example of the mRNA Sar-COV-2 vaccine. This disclosure details the synthesis and evaluation of novel silyl-containing lipid structures to access innovative cationic lipid structures representing new chemical space for biomedical research.

FIGS. 1A and 1B show an example in which a silicon atom in the form of a silyldimethyl or silylcycloakyl group are incorporated into the target lipid DOTMA (1,2-di-O-octadecenyl-3-trimethylammonium-propane) in place of a carbon-carbon double bond. The position of the silicon atom on the lipid tail, the option of branching the tail at the silicon atom, and the ability to use different headgroups represents a modular design by which the user may optimize lipid properties for a chosen purpose. Silyl LNPs containing, for example, a therapeutic RNA molecule has higher transfection efficacy, wide cell tolerability, and a longer shelf life.

FIG. 2 is a scheme of chemical reagents and synthesis, whereby several families of molecular building blocks and precursors are used to produce silyl lipids with a silicon atom placed at a precise location in the lipid structure. Different metal catalysts can be used for hydrosilylation reactions, where the catalyst is selected based on the yield and isomeric purity of the silylated lipid product. The synthesis also has flexibility since the hydrosilylation step can be performed in a different order to access the lipid structures.

Three classes of cationic silyl-lipids may be synthesized in modular fashion to access structural and conformational cationic lipid analogs that have implications in the phase transition temperature and the fluidity of the bilayer, influencing the stability, toxicity, and fusogenicity of silyl-LNPs. This technology is focused on the synthesis of novel silyl-containing lipids as diverse cationic lipid vectors using catalytic hydrosilylation methods, particularly focusing on the modular incorporation of a silyl dimethyl group as a bioisostere of a cis carbon-carbon double bond of known unsaturated cationic lipid vectors, as well as other silyl groups with relevant properties to modulate the branching and chain length of the resulting lipid. Target molecules include silyl analogs of DOTMA, DOTAP (N-(1-(2,3-dioleoyloxy) propyl)-N,N,N-trimethylammonium chloride) and DOSPA (2'-(1", 2"-dioleoyloxypropyldimethyl-ammonium bromide)—N-ethyl-6-amidospermine tetratrifluoroacetic acid).

Use of Silyl-Lipid Containing LNPs for Drug Delivery

Unsaturated and branching fatty acid chains have shown to provide a fluidity to the bilayer by disrupting membrane packing, facilitating endosomal escape and oligonucleotide delivery. Cationic and ionizable lipid vectors, including DOTMA, DOTAP, DOSPA and DLin-MC3-DMA lipids, are examples of optimized cis-unsaturated lipids for improved transfection efficiency but a disadvantage to incorporating unsaturation is cis-trans isomerization of alkenes and susceptibility to oxidation, leading to low stability in storage and compatibility with diverse cell types.

Silanes and siloxanes have been incorporated into synthesized products in other fields, such as materials and inorganic chemistry. This disclosure shows that unique properties of silicon can be exploited for biomedical applications. The flexible steric and substitution patterns of silyl groups allow tunable reactivity, stability, and solubility.

Some of the properties relevant for medicinal and clinical applications are the following:

1. The C—Si bond is stable under physiological conditions;
2. There is no known inherent "element-specific" toxicity of silicon containing compounds;
3. The silicon atom has a larger covalent radius with 20% longer Si—X bonds, compared with C—X bonds, and provides higher conformational flexibility;
4. The electropositive nature and bond-polarization of silicon (relative to C, N, O) contributes to an electron-deficient center;
5. Trialkylsilyl groups are more lipophilic than the corresponding trialkylmethyl groups (Log P for trimethylsilyl-benzene=4.7 vs Log P for t-butylbenzene=4.0); and
6. Silicon can prevent or alter oxidative metabolism and metabolic fate to avoid toxic metabolites.

Structure of Silyl Lipids

Silyl lipids of this disclosure typically are amphipathic, having a charged headgroup, and one, two, or more than two lipophilic tails. The silicon atoms are located in the tails, taking the place of one or more cis alkene groups of previously known unsaturated fatty acids, or otherwise imparting solubility characteristics in a lipid monolayer or bilayer of interest to the user.

Particular silyl lipids in this class may be depicted as shown in Formula I:

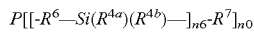

Formula I

When $R^6$ and $R^7$ are saturated allylene and alkyl groups respectively, this may be written as shown in Formula II:

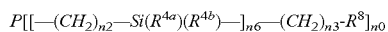

Formula II

P is a polar headgroup, typically containing 2 to 25 or more carbon atoms and 2 to 8 or more oxygen atoms. It is a hydrocarbon that is saturated or unsaturated and substituted or unsubstituted, and optionally contains a cyclic hydrocarbon or aromatic substituent. It may also contain least one nitrogen atom that is ionizable or positively charged; and/or a phosphate (=$OPO_3$). When used to form lipid nanoparticles, $R^{4a}$ and $R^{4b}$ are usually selected from methyl and a linear alkyl group of at least 4 carbon atoms.

n6 is the number of silicon atoms per lipid tail. It is typically an integer between 1 and 4. If n6>1, then n2, $R_{4a}$, and $R_{4b}$ in each section of the tail may be the same or different. n0 is the number of lipid tails per lipid molecule, typically an integer between 1 and 8. In Formula I, $R^6$ and $R^7$ are an alkylene or alkyl group respectively of 2 to 12 carbon atoms, typically linear but optionally branched, typically saturated but optionally unsaturated. Optionally, each of the tails may independently have a non-linear end group $R^8$, which may be a substituted or unsubstituted hydrocarbon. For each of the lipid tails, $R^7$ in Formula I and $R^8$ in Formula II may be the same or different. n6 (the number of silicon atoms per lipid tail) is between 1 and 4; and n0 (the number of lipid tails per lipid molecule) is between 1 and 6. In both Formula I and Formula II, $R^{4a}$ and $R^{4b}$ together may form a silicon substituted cyclical hydrocarbon, for example, in the form —Si(=$(CH_2)n$)—, where n is between 2 and 6, typically 3 or 4.

In Formula II, n2 and n3 (the number of methylene groups surrounding each silicon atom) are typically from 2 to 12. $R^{4a}$ and $R^{4b}$ may both be methyl, in which case the fatty acid forms a single chain with an internal —$CH_2$—Si($CH_3$)$_2$—$CH_2$—. Alternatively, one or more of the lipids may have branched fatty acid tails, wherein at least one of $R^{4a}$ and $R^{4b}$ is a linear saturated or unsaturated hydrocarbon of at least 2, 4, or 8 carbon atoms. If n0>1, the lipid tails may be identical or different.

Some lipids useful for making LNPs have the structure shown in Formula III:

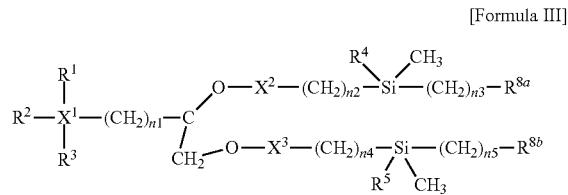

[Formula III]

The group ($R^1$,$R^2$,$R^3$)—represents the charged headgroup, which is linked in this example to a glycerol or acyl glycerol bearing two fatty acids. In this example, $R^1$, $R^2$, and $R^3$ are independently H, —$CH_3$, or a substituted or unsubstituted hydrocarbon containing two to ten carbon atoms or more, optionally containing cyclical or aromatic substituents. Typically $X^1$ is nitrogen, but it may also be phosphate, which case the silyl lipid is a phospholipid.

The headgroup (being the hydrophilic portion) may be charged or uncharged. Lipids that are permanently cationic can be formed, for example, by making $X^1$ a quaternary nitrogen, wherein each $R^1$, $R^2$, and $R^3$ contains at least one carbon atom: for example, the silyl equivalent of 1,2-di-O-octadecenyl-3-trimethylammonium-propane (DOTMA), or 1,2-dioleoyl-3-trimethylammonium-propane (DOTAP). If at least one of $R^1$, $R^2$, and $R^3$ is hydrogen, the molecule will be ionizable, which means that the lipid will be protonated at low or moderate pH to a positive form. In some instances, ionizable lipids are beneficial for mRNA delivery in vivo, because neutral lipids have less interactions with anionic membranes of blood cells, thereby improving biocompatibility.

If $X^1$ is phosphate, a negatively charged substituent is included to the headgroup. If this is the only charged substituent, then the lipid will be negatively charged or anionic at neutral pH. The lipid may contain both a phosphate at position and an ionizable nitrogen as part of $R^1$, $R^2$, or $R^3$. In this case, the headgroup and the lipid will be at least zwitterionic, being neutral, positive, or negatively charged depending on other ionizable groups that may also be present as part of the headgroup structure. An example is a silylated form of 2-dioleoyl-sn-glycero-3-phosphoethanolamine (DOPE), namely Silyl-DOPE, shown in FIG. 4.

As depicted in Formula III, $X^2$ and $X^3$ are independently methylene or carboxyl, or together constitute a quaternary carbon. $R^4$ and $R^5$ are independently selected from methyl and a linear alkyl group of 4 to 12 carbon atoms. n1 (the number of carbon atoms in the link between the headgroup and the fatty acid portion) is often 1 or between 1 and 4 or 1 and 8, inclusive. With respect to each of the lipophilic tails—that is to say, $[[—R^6—Si(R^{4a})(R^{4b})—]_{n6}-R^7]$ in Formula I, $[[—(CH_2)_{n2}—Si(R^{4a})(R^{4b})—]_{n6}—(CH_3 \text{ or } —R^8]$ in Formula II, or $[—(CH_2)_{n2}—Si(R^4)(CH_3)—(CH_2)_{n3}—CH_3$ or $—R^{8a}]$ and $[—(CH_2)_{n4}—Si(R^5)(CH_3)—(CH_2)_{n5}—CH_3$ or $R^{8b}]$ in Formula III or IIIa—n2, n3, n4 and n5 are independently 4 to 12. $R^{8a}$ and $R^{8b}$ are independently methyl or a saturated or unsaturated hydrocarbon of 2 to 10 carbon atoms.

By way of illustration, $R^1$, $R^2$, and $R^3$ in Formula III may all be $—CH_3$, or $R^1$ and $R^2$ are both $—CH_3$ while $R^3$ is an alkyl or heteroalkyl group containing two to ten carbon atoms. In Formula III, $X^2$ and $X^3$ may be independently methylene or carbonyl. In some of the examples shown in the drawings, n2 and n4 are both 7, and n3 and n5 are both 7. The silicon atom in each fatty acid may be blocked, herein $R^4$ and $R^5$ are both methyl.

Alternatively, each of the tails may branch at the silicon atom into a second tail, wherein one or other or both of $R^4$ and $R^5$ are independently a linear alkyl group of 4 to 12 or 6 to 10 carbon atoms.

An included is a variant of Formula III incorporating a silicon substituted carbocycle, such as silicon substituted cyclobutane, cyclopentane, or cyclohexane. This is depicted in Formula IIIa, where n is 0 to 4, typically 1 or 2.

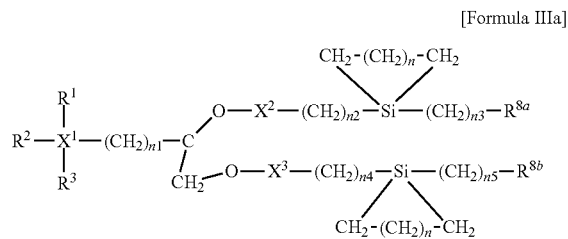

[Formula IIIa]

Figure 4:
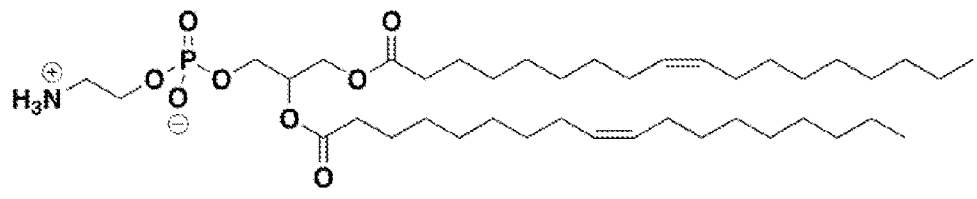
Figure 4:
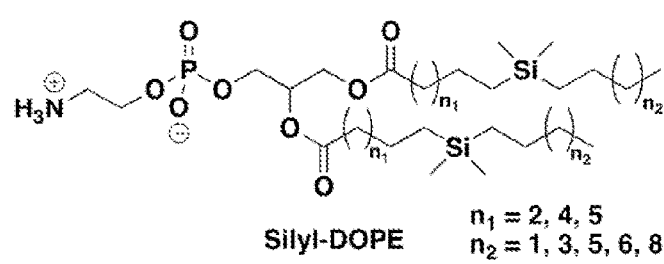
Figure 4:
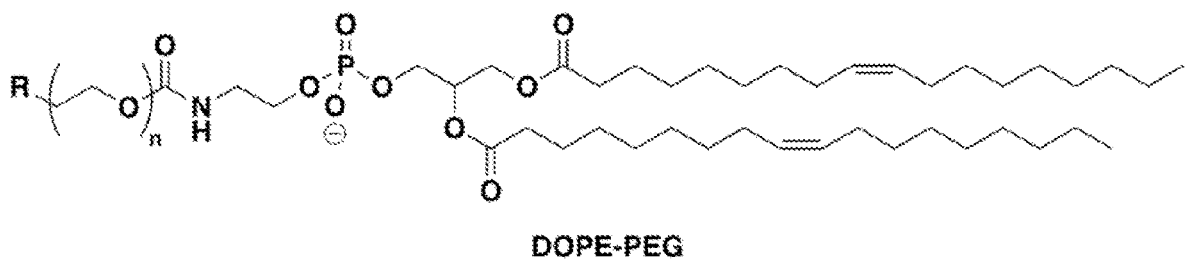
Figure 4:
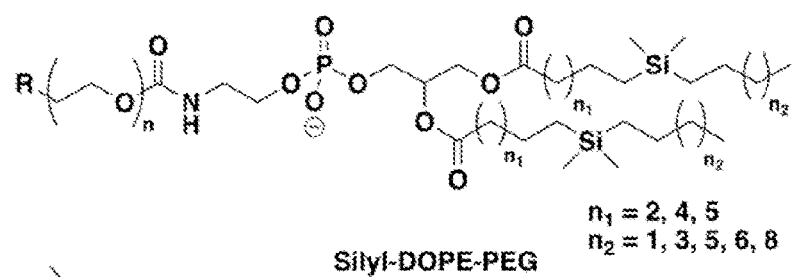
Figure 4:
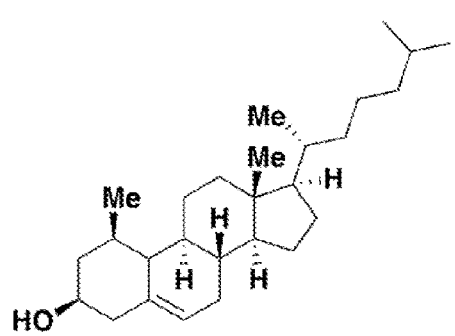
Figure 4:
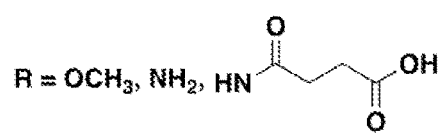

FIG. 4 depicts PEGylated forms of both DOPE and Silyl-DOPE. Included as part of this disclosure are PEGylated forms of any of the silyl lipids put forth herein. A "PEGylated" lipid is a lipid that has a polyethylene glycol substituent contained in or covalently lined to the head group.

Referring to Formulas III and IIIa, any one or more of $R^1$, $R^2$, and $R^3$ contain $—O—[CH_2—CH_2—O—]_{n9}—R^9$. The substituent $R^9$ is $—OH$, $—OCH_3$, $—NH_2$, or a substituted hydrocarbon (usually charged, ionizable, or otherwise polar). n9 is an integer of 10 or more, typically between 10 and 1000, rendering silyl lipids that are between approximately 500 Da and 40,000 Da in weight. Also contemplated are PEGylated silyl lipids containing in their headgroups a polyethylene glycol or equivalent thereof that is branched, Y shaped or comb shaped. Silyl lipids have low dispersion and are typically amphipathic (soluble in both polar and nonpolar solvents). They are generally non-toxic and biodegradable.

Procedures for LNP Preparation

Any suitable process to prepare LNP may be used, such as high shear homogenization and ultrasound, solvent emulsification/evaporation, or microemulsion. General methods for preparing nanoparticles are described, for example, in U.S. Pat. No. 9,393,215 (Glaxo Smith-Klein) and U.S. Pat. No. 10,266,485 (Moderna). The nanoprecipitation method and solvent displacement method are described in U.S. Pat. No. 5,049,322.

A polymer is dissolved in an organic solvent such as acetone or ethanol. The resulting organic solution is combined with a further solvent, which is miscible with the organic solvent while being a non-solvent for the polymer, typically an aqueous solution such as deionized water, normal saline, or a buffered solution. A surfactant may also be present.

The organic solution and aqueous solutions are then combined in suitable relative volumes. For example, the organic solution may be poured or injected into the non-solvent while stirring, or vice versa. By selecting a system in which the polymer is soluble in the organic solvent, while being significantly less soluble in the miscible blend of the organic solvent with the non-solvent, a suspension of nanoparticles may be formed virtually instantaneously. Subsequently, the organic solvent can be eliminated from the suspension, for example, by evaporation under ambient conditions or evaporation under reduced pressure and/or elevated temperature. Pharmaceutical agents may be added to the organic solution, if in oil-soluble or oil-dispersible form or to the aqueous solution, if in water-soluble or water-dispersible form.

Surfactants useful for making lipid nanoparticles include various detergents, dispersing agents, suspending agents, and emulsion stabilizers. The amount of surfactant will be effective to promote acceptable nanoparticle suspension (and resuspension after lyophilization).

Cryoprotective agents can be added to the compositions to prevent nanoparticle agglomeration from occurring when lyophilized compositions in accordance with the invention are resuspended. Depending on the LNP formulation, suitable cryoprotective agents may include amino acids such as glutamic acid and arginine; polyols, including diols such as ethylene glycol, and/or carbohydrates (monosaccharides, disaccharides, polysaccharides such as cellobiose; and alditols such as xylitol and sorbitol.

Features of Lipid Nanoparticles Containing Silyl Lipids

A lipid nanoparticle may be a lipophilic or amphipathic core containing a drug payload, coated with a single lipid layer. Alternatively, it may be a liposome or other multilamellar particle comprising a lipid bilayer with the drug payload enveloped inside.

The LNP may contain any percentage of silyl lipids that is useful. LNPs may be characterized in terms of the percentage of lipids in a preparation that are silyl lipids, and the percentage of silyl lipids that have a particular property. Unless specified otherwise, a silyl LNP preparation of this disclosure will have a lipid composition in which at least 5% of the lipids are silyl lipids, and at least 5% of the silyl lipids are ionizable or cationic (percent per mole). Other useful ranges are LNPs wherein at least 2%, 10%, 20%, or 50%, or between 1% and 50% or 5% to 30% of the lipid molecules are silyl lipids; and at least 10%, 20%, or 50%, or between 1% and 50% or 5% to 30% of the silyl lipid molecules are ionizable and/or cationic (percent per mole).

In addition to cationic or ionizable lipids, LNP formulations may contain other lipid components. Lipids for optional inclusion include triglycerides, diglycerides, monoglycerides, fatty acids, steroids, and waxes. The non-silyl lipids may be saturated or unsaturated. Included are naturally occurring or artificial phospholipids (for example, phosphatidylcholine and phosphatidylethanolamine), and polyethylene glycol (PEG)-functionalized lipids. These may be included, for example, to improve nanoparticle properties, such as particle stability, delivery efficacy, tolerability and biodistribution. Alternatively or in addition, a sterol such as cholesterol or a derivative thereof may be included in the LNP preparation to enhance particle stability by modulating membrane integrity and rigidity. Exemplary inclusions in LNPs of this disclosure are artificial lipids that are known to create pharmaceutically valuable LNPs, such as DOTMA, DOPE, DOTAP, or any of the lipids described in the article by X. Hou et al., Nat Rev Materials 2021, 10:1-17, or in U.S. Pat. Nos. 9,393,215 and 10,266,485 that are not silylated. The lipid balance in the LNP preparation is chosen to achieve satisfactory delivery efficacy and biodistribution of the pharmaceutical agent.

Included as part of this disclosure are lipid nanoparticles that comprise three types of lipid components together—each serving a unique role in transfection and delivery. Any one or two of these, or all three of which may include a proportion that is silylated. The three-component formulation can be used to enhance transfection and delivery of the lipid nanoparticles and their cargoes. The three components are cationic lipids (such as DOTMA and DOTAP), ionizable lipids (such as DOPE) and PEGylated lipids. Cholesterol is optionally included as a forth component.

Cationic lipids have a permanent positive charge and facilitate in the encapsulation of RNA during lipid nanoparticle formation. Ionizable lipids can be protonated or deprotonated at the amine position depending on pH. These ionizable lipids facilitate in endosomal escape of the RNA by becoming protonated in the endosome after cellular uptake and promoting the Hexagonal II phase conformation. PEGylated lipids may increase the structural stability of nanoparticles made therefrom, improving blood circulation time and biodistribution of the nanoparticles. Cholesterol is used to maintain the structural stability of the lipid nanoparticles.

An LNP designed and manufactured in accordance with this technology is typically spherical with an average diameter between 10 and 1000 nanometers. Working size range will depend on the method of manufacture, and the intended stability and clinical effect. Working ranges for solid nanoparticles or liposomes are, for example, at least 10, 20, 50, 100, or 200 nm in diameter, no more than 50, 100, 200, or 500 nm in diameter, or between 20 and 500 nm, 10 and 200 nm, or 100 and 500 nm.

The choice of a particular silyl lipid used, its structure, the proportion of silyl lipids to non-silyl lipids, and other features potentially affect the properties of nanoparticles made therefrom: for example, yield, particle size, zeta potential, membrane fusion, deliverability of a drug payload, and effectiveness as a delivery vehicle in vivo. All these variables can be optimized by empirical testing.

For colloidal dispersions, zeta potential is a useful measurement of the difference in electrokinetic potential between the dispersion medium and the stationary layer of fluid attached to the dispersed particle. The magnitude of the zeta potential indicates the degree of electrostatic repulsion between adjacent, similarly charged particles in a dispersion. A high zeta potential is an indicator of stability (resistance to aggregation). Both zeta potential and size can be determined using a zeta Potential Analyzer. Clogston JD et al., Methods Mol Biol. 2011;697:63-70.

Figure 5B:
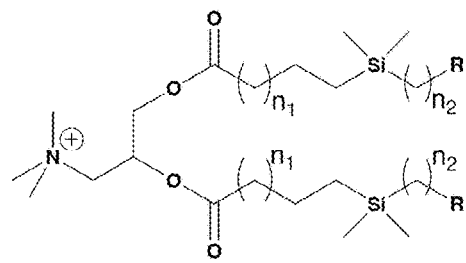
Figure 5B:
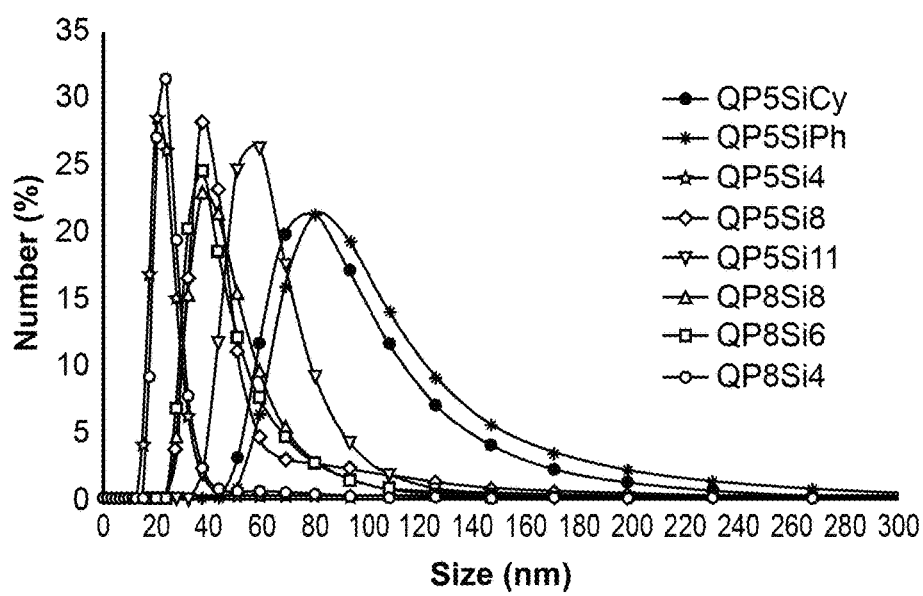
Figure 5C:
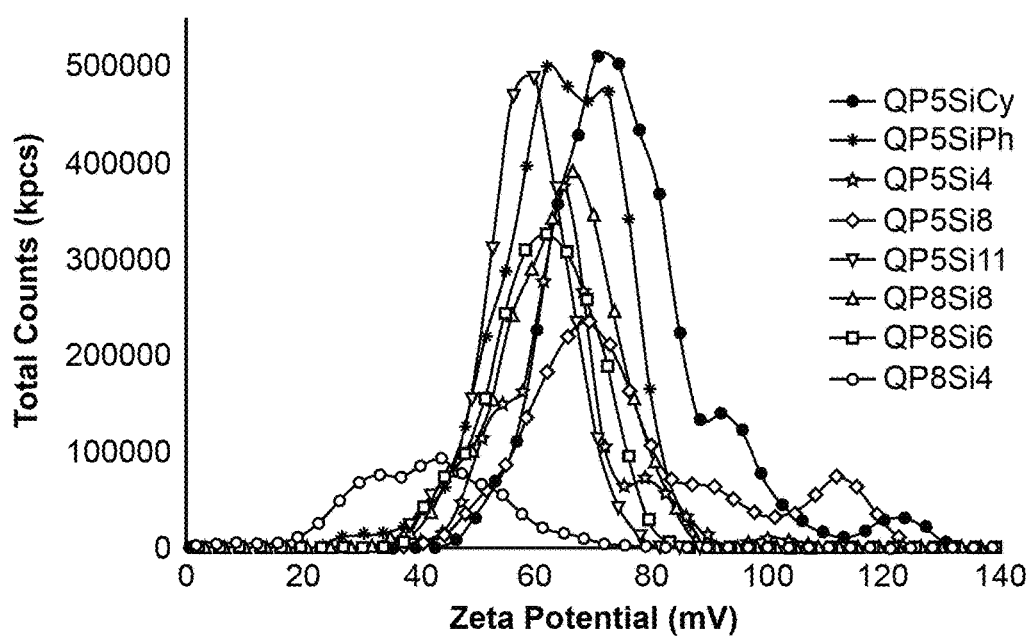

FIGS. 5A to 5C and TABLE 1A provide an illustration of such empirical determination: the effect of the length of the lipid tail, the end group, and the positioning of the silyl group. In this illustration, other properties of the lipid structure and liposome composition were kept constant. The liposome formulations just contained the cationic silyl lipids indicated, and Milli Q™ purified water.

TABLE 1A

Cationic silyl lipid structures and the effect on nanoparticles produced

| Preparation | n1 | n2 | R | Yield (%) | Avg. Size (nm) | Avg. zeta Potential (mV) |
|---|---|---|---|---|---|---|
| QP5SiCy | 2 | 0 | Cyclohexyl | 42 | 80 | 71; 124 |
| QP5SiPh | 2 | 0 | Phenyl | 39 | 80 | 62 |
| QP5Si4 | 2 | 3 | $CH_3$ | 52 | 21 | 65 |
| QP5Si8 | 2 | 7 | $CH_3$ | 25 | 38 | 69; 112 |
| QP5Si11 | 2 | 10 | $CH_3$ | 22 | 59 | 60 |
| QP8Si8 | 5 | 7 | $CH_3$ | 7 | 38 | 67 |
| QP8Si6 | 5 | 5 | $CH_3$ | 6 | 38 | 62 |
| QP8Si4 | 5 | 3 | $CH_3$ | 9 | 24 | 33; 44 |
| QP7Si9 | 4 | 8 | $CH_3$ | 4 | 59 | 74 |
| QP8SiCy | 5 | 0 | Cyclohexyl | 48 | 29 | 57; 71 |
| QP8SiPh | 5 | 0 | Phenyl | 46 | 21 | 59; 73 |

FIG. 5A and the first four columns of TABLE 1A show the choices made as to the structure of the lipid. FIGS. 5B and 5C graph the results. There was a substantial effect of these input parameters on yield, particle diameter, and zeta potential.

In some circumstances, putting a more bulky hydrophobic group such as cyclohexyl and phenyl at the end of the lipid tail may have the following benefits:

(1) decrease the length and hydrodynamic diameter of the silyl-LNPs resulting in a smaller LNP for RNA delivery that is more able to get inside the cell via endocytosis, and (2) disrupt lipid tail packing and promoting endosomal escape of RNA inside the cell resulting in increased transfection efficiency. The cyclohexyl or phenyl group may also help to fine tune interactions between lipid tails that are relevant for fluidity, such as potential pi-pi stacking interactions of the phenyl rings.

Figure 6:
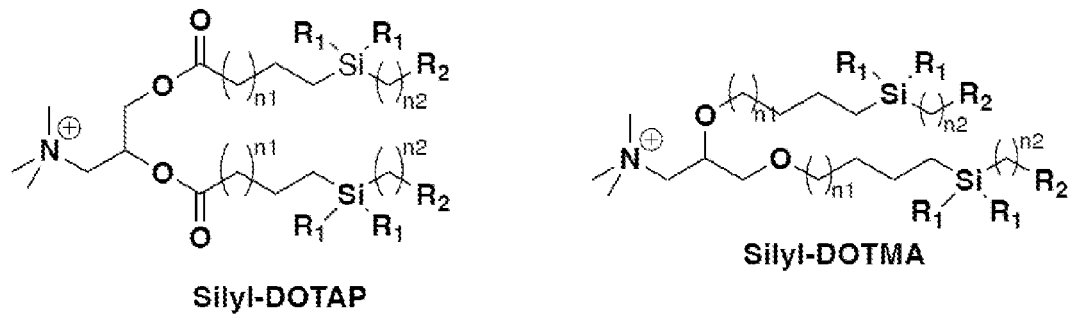
Figure 6:
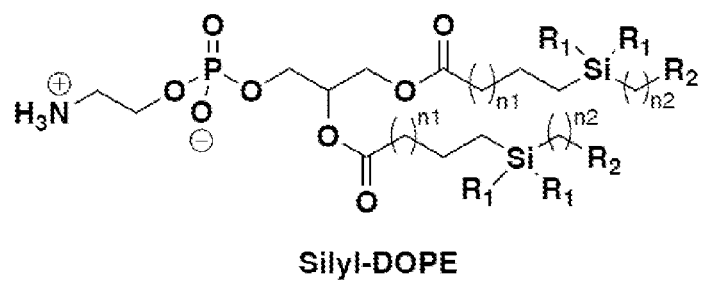
Figure 6:
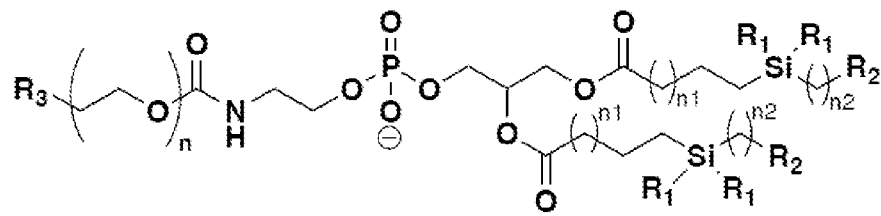
Figure 6:
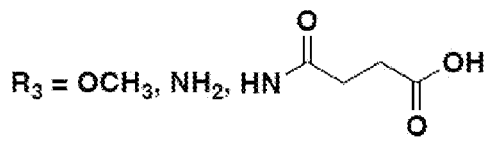
Figure 6:
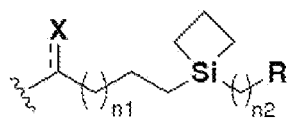

FIG. 6 shows some examples of possible alternatives to —$CH_3$ placed at or near the lipid tail of silyl lipids to instill nanoparticles made therefrom with such advantages.

Figure 7A:
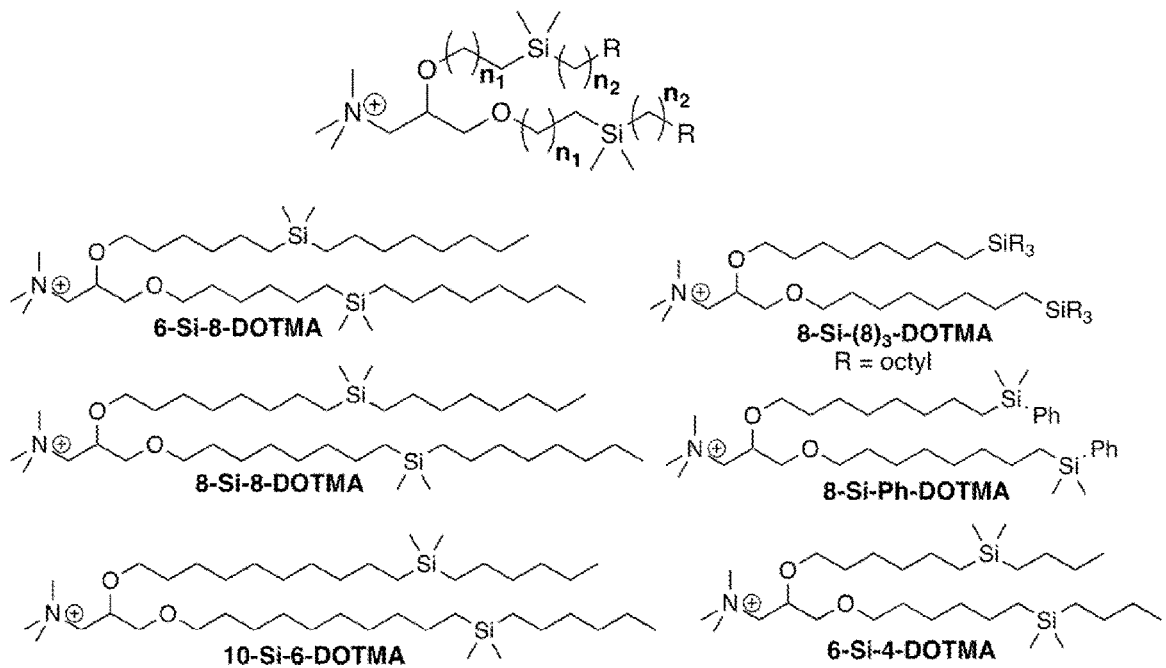
Figure 7B:
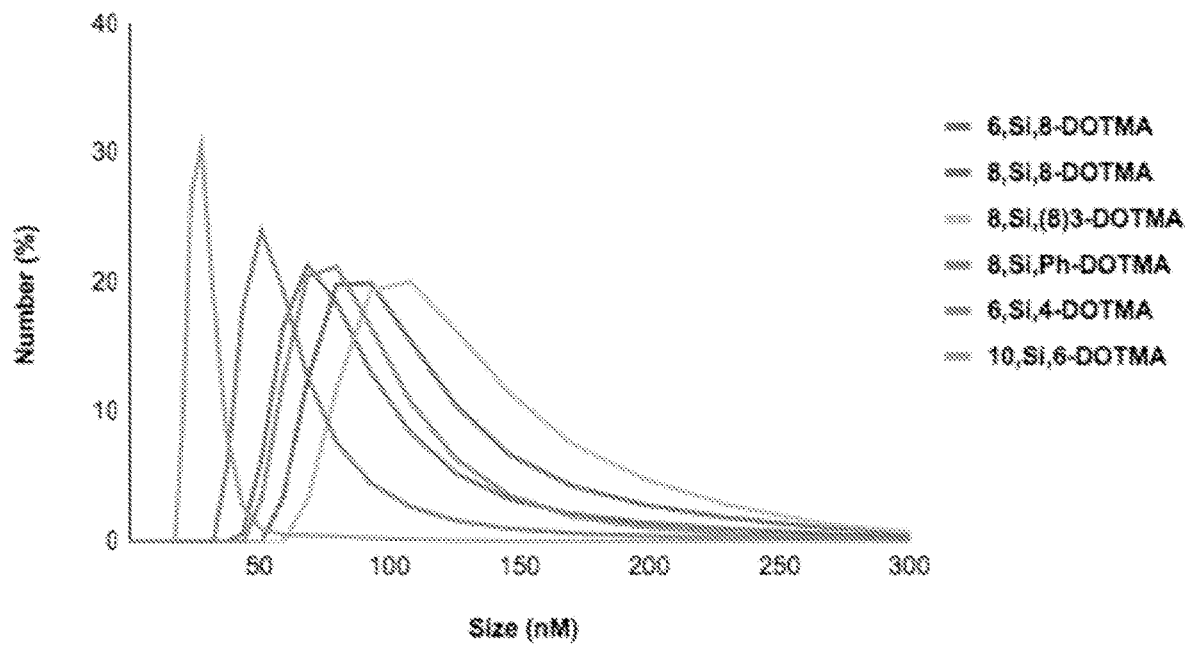

FIGS. 7A to 7C and TABLE 1B provide another illustration of how structure of the silyl lipid can affect properties of nanoparticles.

TABLE 1B

Cationic silyl lipid structures and the effect on nanoparticles produced

|  | n1 | n2 | R | Avg size (nm) | Avg. zeta potential (mV) |
|---|---|---|---|---|---|
| 6,Si,8-DOTMA | 5 | 7 | $CH_3$ | 216 | 64 |
| 8,Si,8-DOTMA | 7 | 7 | $CH_3$ | 206 | 56; 74 |
| 8,Si,(8)$_3$-DOTMA | 7 | 7 | $CH_3$ | 184 | 64 |
| 8,Si,Ph-DOTMA | 7 | 0 | $CH_3$ | 215 | 62 |

TABLE 1B-continued

Cationic silyl lipid structures and
the effect on nanoparticles produced

| | n1 | n2 | R | Avg size (nm) | Avg. zeta potential (mV) |
|---|---|---|---|---|---|
| 6,Si,4-DOTMA | 5 | 3 | Phenyl | 79 | 65 |
| 10,Si,6-DOTMA | 9 | 5 | $CH_3$ | 65 | 52 |

(DOTMA)/cholesterol liposome size: 126 nm
(DOTMA)/cholesterol zeta potential: 51 mV Six synthesized sila-DOTMA analogs were found to be capable of forming liposomes with similar size and zeta potential compared with native DOTMA. Structural features such as tail length, positioning of the silicon group (n1, n2), and branching (as in 8,Si,(8)$_3$-DOTMA) can influence liposome properties.

Adaptation of Previous LNP Technology Using Silyl Lipids

To implement this technology in other ways, the user is not constrained to particular formulas, structures, or named compounds referred to in this disclosure. They may be guided instead by empirically adjusting or optimizing the structure in silico and/or by experimentation in vitro.

Figure 3A:
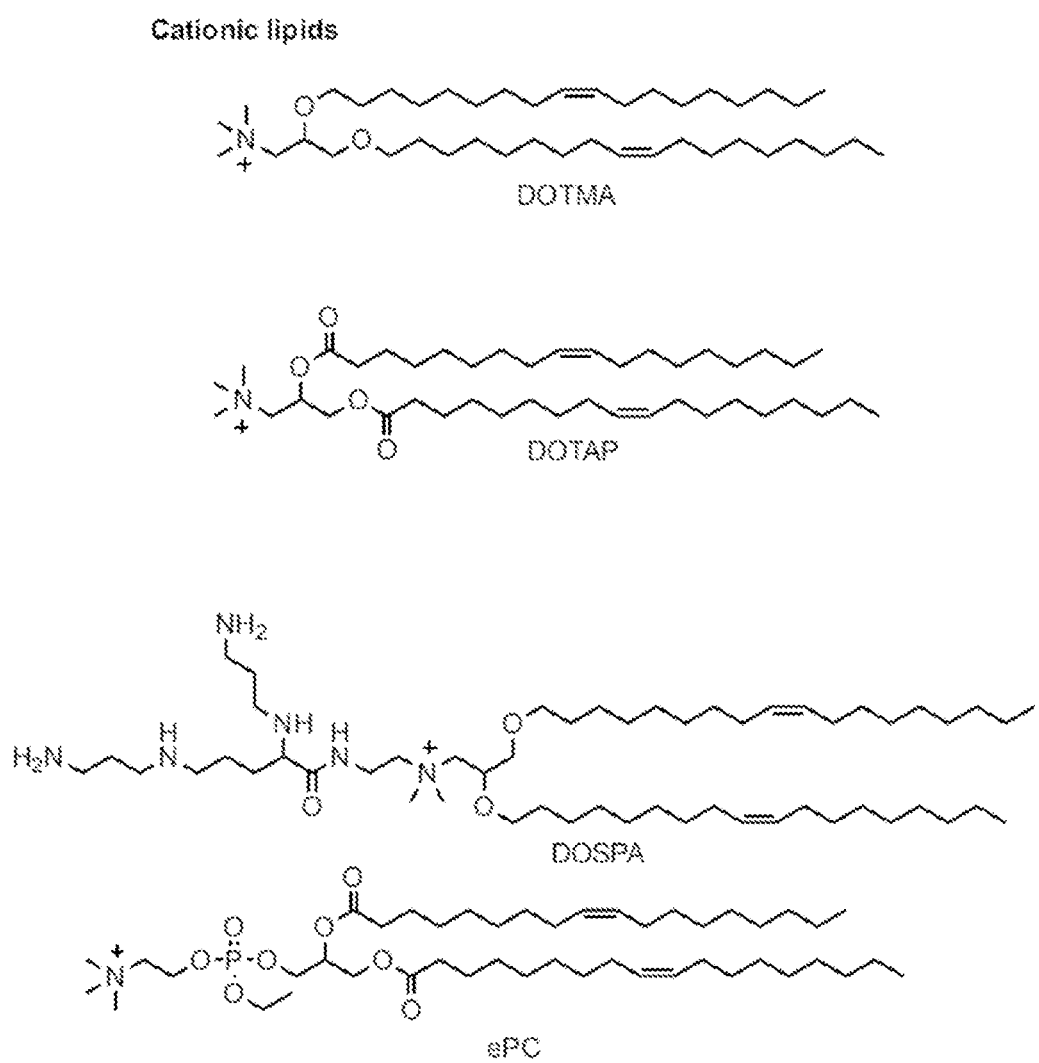
Figure 3B:
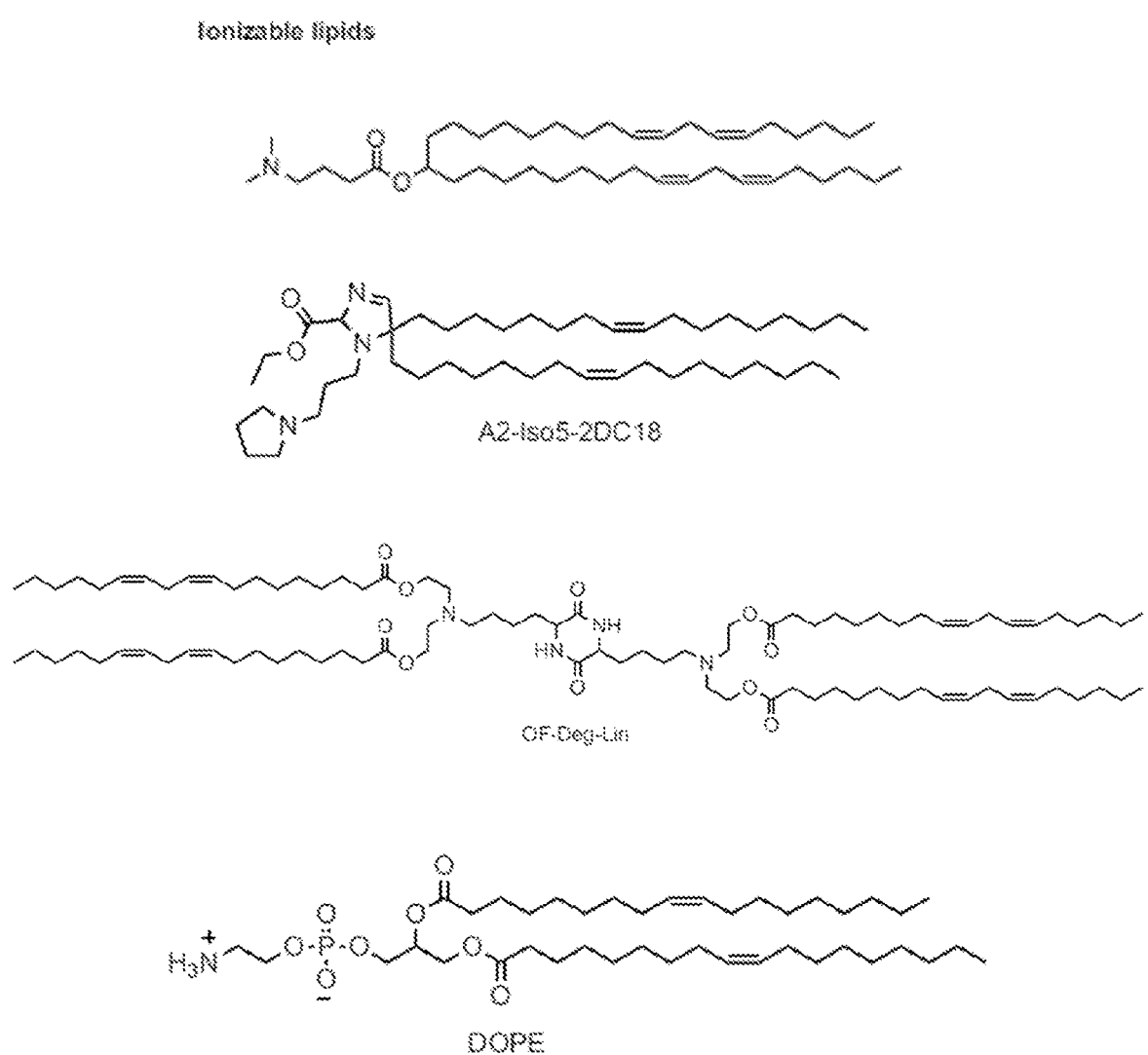

FIGS. 3A and 3B show lipids that have been developed or shown to be effective in imparting LNPs with particular properties. Any known lipid or lipid-like structure can be used as a starting model for the development of silyl lipids and silyl LNPs. For example, a silicon linkage in the form of [—$CH_2 \leq Si(R^{4a})(R^{4b})$—$CH_2$—], [—($CH_2$)—$Si(CH_2)$ ($R^4$)—$CH_2$—], [—($CH_2$)—$Si(CH_2)_S$—$CH_2$—], or —$CH_2$—$Si$(—$CH_2$—($CH_2$)$_n$—$CH_2$—)—$CH_2$— (where n is 0 to 4) may be inserted into a fatty acid tail or linear alkyl group (saturated or unsaturated) at any place that is desired.

One approach to improve a previously designed or characterized preparation of lipid nanoparticles is to determine lipids contained in the previous preparation that have one or more cis-unsaturated carbon-carbon bonds in one or more fatty acids in the lipid; substituting —$Si(CH_3)_2$— or —$Si$(—$CH_2$—($CH_2$)$_n$—$CH_2$—)— for one or more of the cis-unsaturated carbon-carbon bonds to produce a silyl lipid; and producing an improved preparation of lipid nanoparticles that contain the silyl lipid. Any of the lipids shown in FIGS. 3A and 3B can be converted to silyl counterparts in this fashion.

Characterization of Silyl-Lipid Containing LNPs

The biophysical properties of novel silyl LNPs are measured for liposome formation and silyl-LNP formulation and established through characterization techniques including measurements of zeta potential, transmission electron microscopy and small-angle X-ray scattering. The RNA/silyl-LNP complex is characterized using HPLC to quantify RNA encapsulation. In cellulo studies can compare transfection efficacy of siRNA and cytotoxicity of silyl-lipid LNPs with commercially available liposome RNA delivery systems.

Pharmaceutical Payloads and Therapeutic Applications

Silyl lipid containing lipid nanoparticles according to this disclosure can be used for delivering any pharmaceutical payload in vivo that the clinician or investigative scientist may wish to use. Suitable are small molecule pharmaceutical agents (less than 100 Da), proteins, and nucleic acids of various kinds, or a combination thereof. Treatment is done by administering to a subject an amount of the agent-carrying LNPs that is effective in achieving one or more clinical aims. Packaging the pharmaceutical agent in a silyl LNP may enhance stability of the agent or composition during storage, and/or help promote endocytosis or other entry of the pharmaceutical agent into a target cell in a treated subject.

Silyl LNPs are particularly advantageous for delivering a nucleic acid or mixture thereof for purposes of immunization or gene therapy. Illustrative payloads for immunogenic compositions or vaccines are shown in TABLE 2, exemplified by mRNA vaccines. The nucleic acid encodes one or more epitopes from the intended immune target, and optionally one or more proteins that may act as an adjuvant or stimulant to enhance immunogenicity. The target may be an infectious agent, such as a pathogenic virus, bacteria, or protozoan. Alternatively, the target may be a cancer cell, in which case the encoded epitopes are epitopes expressed by the cancer cell that are specific to the cancer or to the tissue type.

For example, the technology of this disclosure can be used to prepare a composition to induce a response to the SARS-CoV-2 virus, for the purpose of prevention or treatment of COVID-19. Representative immunogenic epitopes may be taken from any one or more of the four SARS-CoV-2 structural proteins: namely, membrane glycoprotein (M), envelope protein (E), nucleocapsid protein (N), and the spike protein (S). Most current vaccines against SARS-CoV-2 typically include or encode the whole spike protein. Ways to optimize the spike protein were recently discussed by F. Heinz & K. Stiasny, NPJ Vaccines (2021) 6:104.

TABLE 2

LNP-mRNA immunogenic compositions

| Name | Disease | Encoded antigen | Clinical Trials identifier | Phase |
|---|---|---|---|---|
| Infections | | | | |
| mRNA-1273 | SARS-CoV-2 | Spike | NCT04470427 | III (EUA and CMA) |
| BNT162b2 | SARS-CoV-2 | Spike | NCT04368728 | III (EUA and CMA) |
| CVnCoV | SARS-CoV-2 | Spike | NCT04652102 | III |
| LNP-nCoVsaRNA | SARS-CoV-2 | Spike | ISRCTN17072692 | I |
| ARCT-021 | SARS-CoV-2 | Spike | NCT04728347 | II |
| ARCoV | SARS-CoV-2 | Receptor-binding domain | ChiCTR2000034112 | I |
| mRNA-1440 | Influenza H10N8 | Haemagglutinin | NCT03076385 | I |

TABLE 2-continued

LNP-mRNA immunogenic compositions

| Name | Disease | Encoded antigen | Clinical Trials identifier | Phase |
|---|---|---|---|---|
| mRNA-1851 | Influenza H7N9 | Haemagglutinin | NCT03345043 | I |
| mRNA-1893 | Zika virus | Pre-membrane and envelope glycoproteins | NCT04064905 | I |
| mRNA-1345 | Respiratory syncytial virus | F glycoprotein | NCT04528719 | I |
| mRNA-1653 | Metapneumovirus and parainfluenza virus type 3 (MPV/PIV3) | MPV and PIV3 F glycoproteins | NCT03392389 | I |
| mRNA-1647 | Cytomegalovirus | Pentameric complex and B glycoprotein | NCT04232280 | II |
| mRNA-1388 | Chikungunya virus | Chikungunya virus antigens | NCT03325075 | I |
| CV7202 | Rabies virus | G glycoprotein | NCT03713086 | I |
| Cancer | | | | |
| mRNA-5671/V941 | Non-small-cell lung cancer, colorectal cancer, pancreatic adenocarcinoma | KRAS antigens | NCT03948763 | I |
| mRNA-4157 | Melanoma | Personalized neoantigens | NCT03897881 | II |
| mRNA-4650 | Gastrointestinal cancer | Personalized neoantigens | NCT03480152 | I/II |
| FixVac | Melanoma | NY-ESO-1, tyrosinase, MAGE-A3, TPTE | NCT02410733 | I |
| TNBC-MERIT | Triple-negative breast cancer | Personalized neoantigens | NCT02316457 | I |
| HARE-40 | HPV-positive cancers | HPV oncoproteins E6 and E7 | NCT03418480 | I/II |
| RO7198457 | Melanoma | Personalized neoantigens | NCT03815058 | II |
| W_ova1 | Ovarian cancer | Ovarian cancer antigens | NCT04163094 | I |

The technology of this disclosure can also be used for the purpose of gene therapy, which is the delivery of a nucleic acid to a subject for the purpose of therapy. Therapeutic purposes include but are not limited to expression of a therapeutic protein encoded in the nucleic acid (such as a cytokine or anti-cancer agent), expression of an essential protein that the subject is unable to produce themselves, delivery of a gene editing system such as CRISPR/Cas9 or a guide RNA; or immunization of the subject against a pathogen or antigen encoded in the nucleic acid. Other payloads that can be used for gene therapy include DNA antisense oligonucleotides, DNA aptamers; micro RNAs, short interfering RNAs, ribozymes, RNA decoys and circular RNAs that specifically increase or decrease expression of a particular endogenous gene in the subject or an infectious agent. K. Sridharan et al., Br J Clin Pharmacol. 2016 Sep.; 82(3): 659-672.

Illustrative payloads for gene therapy are shown in TABLE 3. In the examples shown, the nucleic acid encodes a therapeutic antibody (for passive immunization), anti-cancer drugs such as cytokines and chemotactic factors (for cancer treatment), and natural human proteins (to promote synthesis of an essential factor that the subject may be lacking, such as in the case of a genetically inherited condition). TABLES 2 and 3 are adapted from X. Hou et al., Lipid nanoparticles for mRNA delivery, Nat Rev Materials 2021, 10:1-17.

TABLE 3

LNP pharmaceuticals for gene therapy

| Name | Disease | Encoded protein | Clinical Trials identifier | Phase |
|---|---|---|---|---|
| Infections | | | | |
| mRNA-1944 | Chikungunya virus | Antibody against chikungunya virus | NCT03829384 | I |
| Cancer | | | | |
| mRNA 2416 | Solid tumors | OX40L | NCT03323398 | II |
| mRNA-2752 | Solid tumors | OX40L, IL-23 and IL-36γ | NCT03739931 | I |
| MEDI1191 | Solid tumors | IL-12 | NCT03946800 | I |
| SAR441000 | Solid tumors | IL-12sc, IL-15sushi, IFNα and GM-CSF | NCT03871348 | I |

TABLE 3-continued

LNP pharmaceuticals for gene therapy

| Name | Disease | Encoded protein | Clinical Trials identifier | Phase |
|---|---|---|---|---|
| Genetic disorders | | | | |
| mRNA-3704 | Methylmalonic acidaemia | Methylmalonyl-CoA mutase | NCT03810690 | I/II |
| mRNA-3927 | Propionic acidaemia | Propionyl-CoA carboxylase | NCT04159103 | I/II |
| MRT5201 | Ornithine transcarbamylase deficiency | Ornithine transcarbamylase | NCT03767270 | I/II |
| MRT5005 | Cystic fibrosis | Cystic fibrosis transmembrane conductance regulator | NCT03375047 | I/II |
| NTLA-2001 | Transthyretin amyloidosis with polyneuropathy | CRISPR-Cas9 gene editing system | NCT04601051 | I |

Medicaments and Commercial Products

Preparation and formulation of pharmaceutical agents for use according to this disclosure can incorporate standard technology, as described, for example, in the most recent edition of *Remington: The Science and Practice of Pharmacy*. The formulation will typically be optimized for administration systemically, either intramuscularly or subcutaneously, or for administration orally or nasally (for example, to stimulate the mucosal immune system).

Silyl LNP preparations may be provided as one or more unit doses (either combined or separate), each containing an amount of the pharmaceutical payload in LNP form that is effective in the treatment of a chosen disease, infection, or clinical condition. The commercial product may contain a device such as a syringe for administration of the agent or composition in or around the target tissue of a subject in need thereof. The product may also contain or be accompanied by an informational package insert describing the use and attendant benefits of the LNPs in treating the condition for which it is indicated and approved.

Figure 2:
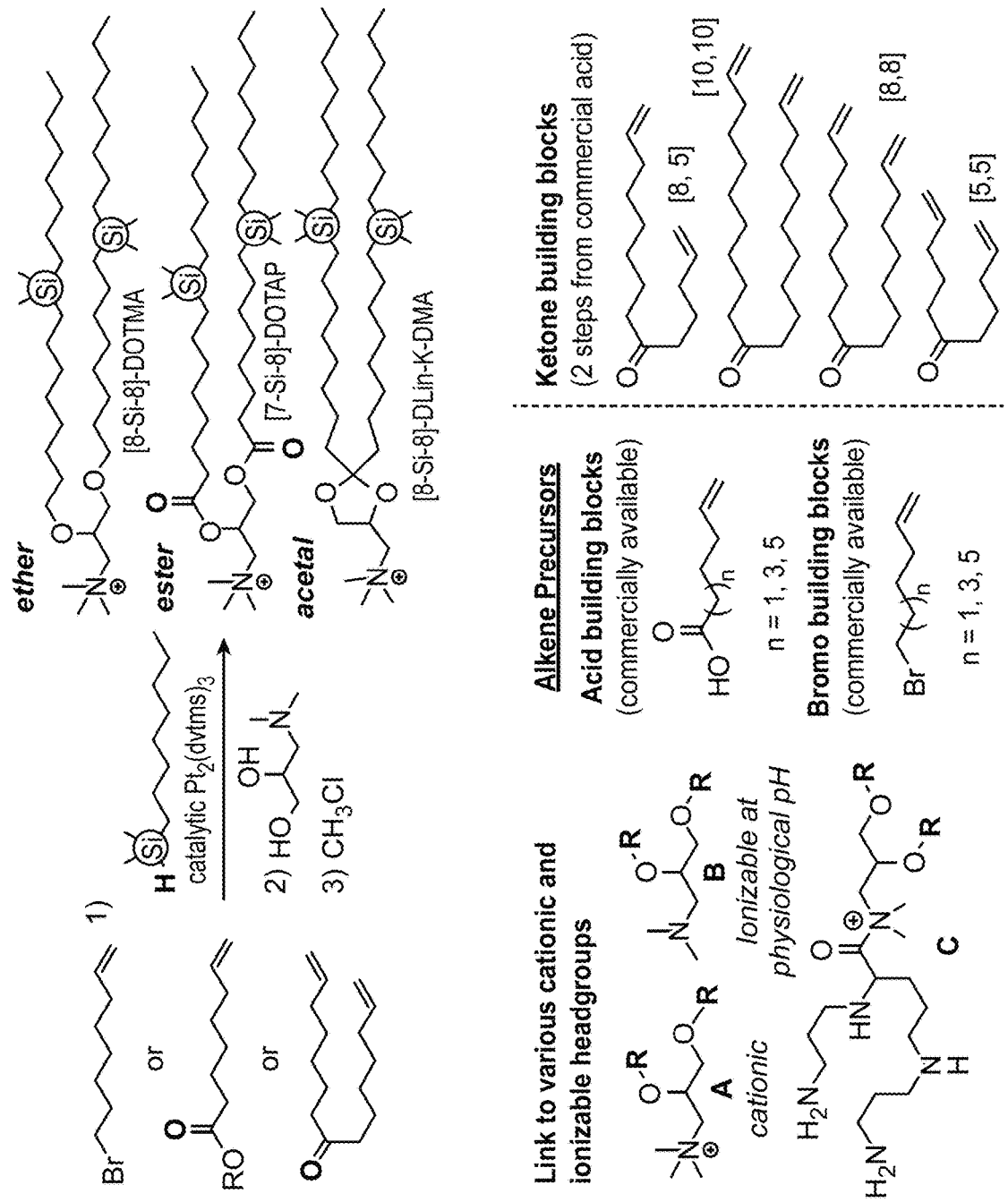
Figure 2:
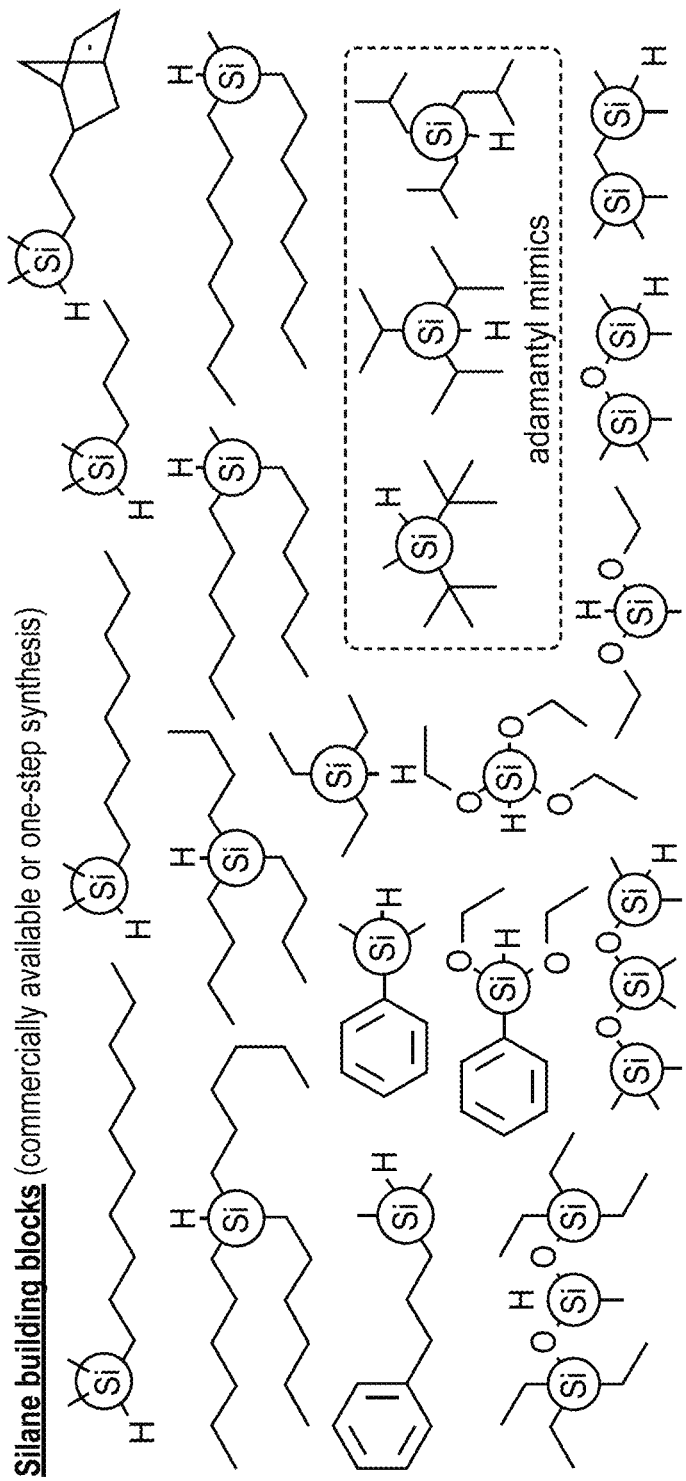

This disclosure also includes kits of chemical compounds, their preparation and use. Such kits may contain a combination of "building blocks" that are useful in constructing or fine-tuning silyl lipids, such compounds selected from what is shown in FIG. 2. Other kits may include preparations of silyl lipids (optionally in combination with emulsion agents) for use in encapsulating a drug or vaccine payload into a silyl LNP preparation as put forth herein.

Terms Used in this Disclosure

The term "lipid" as used in this disclosure refers generally to an organic amphipathic molecule having a charged or ionizable headgroup, and one or more lipophilic tails. The tails are typically linear or branched hydrocarbons, which may be either saturated or unsaturated. The tails may be referred to informally as fatty acids, but this places no constraint on the linkage of the lipophilic tails to the headgroup.

A "lipid nanoparticle" (LNP) is defined as any lipid-containing particle of microscopic or sub-microscopic size, typically but not necessarily less than 1000 nanometers in diameter. LNPs developed for delivery of a therapeutic payload may be (1) a lipophilic or amphipathic solid or liquid core coated with a single lipid layer, (2) a liposome or other particle comprising a lipid bilayer and a solid, liquid, or buffered interior, or (3) a multilamellar structure. The "payload" contains one or more pharmaceutically active compounds (or a placebo equivalent thereof), optionally combined with one or more pharmaceutically acceptable excipients, packing agents, or other compounds.

A "silyl" or "silylated" lipid is a molecule that contains a polar headgroup and one or more alkyl or fatty acid tails. At least one of the tails contains one or more silicon atoms that interconnects portions of the tail. A "silyl LNP" is an LNP in which at least some of the lipids (typically 5% or more wt/wt) are silyl lipids.

In the context of this disclosure, the term "alkyl," by itself or as part of another substituent refers to a straight or branched aliphatic radical having the number of carbon atoms indicated. The term "alkoxy," by itself or as part of another substituent, refers to a group having the formula —OR, wherein R is alkyl. A carbonyl is a C=O group that is divalent at the carbon atom, and double-bonded to an oxygen. The term "alkylene" refers to an alkyl group containing an alkene linking at least two other alkyl groups moieties. The two moieties linked to the alkylene group may be linked to the same carbon atom or different carbon atoms of the alkylene group. The term "alkene" refers to a straight or branched, divalent carbon chain having one or more carbon-carbon double bonds (—CR=CR'—, wherein R and R' are each independently hydrogen or a further substituent). A "cis alkene" contains the structure —CH=CH'— wherein the H atoms are in the cis position. A "heteroalkyl" group is an alkyl group in which one or more of the constituent carbon atoms have been replaced by nitrogen, oxygen, or sulfur. More generally, a "hydrocarbon" (unless otherwise specified) may be linear or branched, saturated or unsaturated, and may contain cycles or aromatic group. A substituted hydrocarbon contains additional atoms that are not carbon or hydrogen in any stable position. Unless otherwise stated or required, other chemical terms have their ordinary meaning.

Unless otherwise stated or required, each of the compound structures referred to in the disclosure include conjugate acids and bases having the same structure, crystalline and amorphous forms of those compounds, pharmaceutically acceptable salts, and prodrugs. This includes, for example, tautomers, polymorphs, solvates, hydrates, unsolvated polymorphs (including anhydrates). For compounds having one or more chiral centers, if an absolute stereochemistry is not expressly indicated, then each center may independently be of R-configuration or S-configuration or a mixture thereof.

A "vaccine" or "immunogenic compound" is a pharmaceutical preparation formulated to initiate an immune response (both B and T lymphocytes) that is specific for a pre-determined antigen or pathogen. It will typically contain or encode one or more epitopes of the antigen or pathogen, packaged in a formulation that is effective in delivering the epitopes to antigen-presenting cells in a subject to which it is administered, which in turn prompts the immune system of the subject to initiate or boost the intended immune response. "Vaccination" or "immunization" is the act of administering such a pharmaceutical composition to a person in need thereof, whether or not they have a particular disease or condition. "Gene therapy" means administering a nucleic acid to a subject in need thereof for the purpose of delivering the nucleic acid in a functional form to a target cell or tissue in the subject for a therapeutic purpose, as described above.

A "therapeutically effective amount" is an amount of a compound of the present disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) at least partially reverses damage caused by the condition prior to treatment.

Successful "treatment" of a condition according to this disclosure may have any effect that is beneficial to the subject being treated. This includes decreasing severity, duration, or progression of a condition, or of any adverse signs or symptoms resulting therefrom. Treatment may also be unsuccessful, resulting in no improvement in typical signs and symptoms of the condition. The subject has still been "treated" if the intention of the managing clinician has been at least in part the improvement or alteration of a condition referred to. A concurrent objective of therapy is to minimize adverse effects on the target tissue or elsewhere in the treated subject.

Published Information

The reader may be guided in their practice of the technology disclosed here by referring to general information and techniques in the following reference texts:

*Solid Lipid Nanoparticles: a Nano Carrier for Drug Delivery* by Sukanta Satapathy, Chandra Sekhar Patro, et al., 2021

*Solid Lipid Nanoparticle: A compendious approaches in industrial scale-up techniques of Solid lipid Nanoparticles and Biomedical applications* by Deep M. K. and Karthikeyan M,2020

*Liposomes: Drug and Gene Delivery Systems (Biomaterials Science)* by Arabinda Chaudhuri, 2022

*The Chemistry of Organic Silicon Compounds*, by Zvi Rappoport and Yitzhak Apeloig, 2001

*Gene Transfer, Gene Therapy And Genetic Pharmacology* by Daniel Scherman, 2019

*Design and Development of Novel Drugs and Vaccine* by Tarun Kumar Bhatt and Surendra Nimesh, 2021

Also potentially of interest are the general information and techniques presented in the following published articles:

Hou X, Zaks T, Langer R, Dong Y. Lipid nanoparticles for mRNA delivery. Nat Rev Materials 2021, 10:1-17.

Schoenmaker, L.; Witzigmann, D.; Kulkarni, J. A.; Verbeke, R.; Kersten, G.; Jiskoot, W.; Crommelin, D. J. A. MRNA-Lipid Nanoparticle COVID-19 Vaccines: Structure and Stability. Int. J. Pharm. 2021, 601 (March), 120586.

Arpicco, S.; Canevari, S.; Ceruti, M.; Galmozzi, E.; Rocco, F.; Cattel, L. Synthesis, Characterization and Transfection Activity of New Saturated and Unsaturated Cationic Lipids. Farm. 2004, 59 (11), 869-878.

Ferrari, M. E.; Rusalov, D.; Enas, J.; Wheeler, C. J. Synergy between Cationic Lipid and Co-Lipid Determines the Macroscopic Structure and Transfection Activity of Lipoplexes. Nucleic Acids Res. 2002, 30 (8), 1808-1816.

Heyes, J.; Palmer, L.; Bremner, K.; MacLachlan, I. Cationic Lipid Saturation Influences Intracellular Delivery of Encapsulated Nucleic Acids. J. Control. Release 2005, 107 (2), 276-287.

Zhi, D.; Zhang, S.; Wang, B.; Zhao, Y.; Yang, B.; Yu, S. Transfection Efficiency of Cationic Lipids with Different Hydrophobic Domains in Gene Delivery. Bioconjug. Chem. 2010, 21 (4), 563-577.

Zhang, Y.; Sun, C.; Wang, C.; Jankovic, K. E.; Dong, Y. Lipids and Lipid Derivatives for RNA Delivery. Chem. Rev. 2021.

Showell, G. A.; Mills, J. S. Chemistry Challenges in Lead Optimization: Silicon Isosteres in Drug Discovery. Drug Discov. Today 2003, 8 (12), 551-556.

Ramesh, R.; Reddy, D. S. Quest for Novel Chemical Entities through Incorporation of Silicon in Drug Scaffolds. J. Med. Chem. 2018, 61 (9), 3779-3798.

Bains, W.; Tacke, R. Silicon Chemistry as a Novel Source of Chemical Diversity in Drug Design. Curr. Opin. Drug Discov. Devel. 2003, 6, 526-543.

Zakai, U. I.; Bikzhanova, G.; Staveness, D.; Gately, S.; West, R. Synthesis of Lipophilic Sila Derivatives of N-Acetylcysteineamide, a Cell Permeating Thiol. Appl. Organomet. Chem. 2010, 24 (3), 189-192.

Gately, S.; West, R. Novel Therapeutics with Enhanced Biological Activity Generated by the Strategic Introduction of Silicon Isosteres into Known Drug Scaffolds. Drug Dev. Res. 2007, 68, 156-163.

Nakamura, M.; Kajita, D.; Matsumoto, Y.; Hashimoto, Y. Design and Synthesis of Silicon-Containing Tubulin Polymerization Inhibitors: Replacement of the Ethylene Moiety of Combretastatin A-4 with a Silicon Linker. Bioorg. Med. Chem. 2013, 21 (23), 7381-7391.

Blakney, A. K.; McKay, P. F.; Yus, B. I.; Aldon, Y.; Shattock, R. J. Inside out: Optimization of Lipid Nanoparticle Formulations for Exterior Complexation and in vivo Delivery of SaRNA. Gene Ther. 2019, 26 (9), 363-372.

Fletcher, S.; Ahmad, A.; Perouzel, E.; Heron, A.; Miller, A. D.; Jorgensen, M. R. In vivo Studies of Dialkynoyl Analogues of DOTAP Demonstrate Improved Gene Transfer Efficiency of Cationic Liposomes in Mouse Lung. J. Med. Chem. 2006, 49 (1), 349-357.

Semple, S. C.; Akinc, A.; Chen, J.; Sandhu, A. P.; Mui, B. L.; Cho, C. K.; Sah, D. W. Y.; Stebbing, D.; Crosley, E. J.; Yaworski, E. Rational Design of Cationic Lipids for SiRNA Delivery. Nat. Biotechnol. 2010, 28 (2), 172-176.

Akinc, A.; Zumbuehl, A.; Goldberg, M.; Leshchiner, E. S.; Busini, V.; Hossain, N.; Bacallado, S. A.; Nguyen, D. N.; A combinatorial approach to determine functional group effects on lipidoid-mediated siRNA delivery. Bioconjug Chem. 2010 Aug. 18; 21(8): 1448-1454.

Rietwyk, S. and Peer, D. Next Generation Lipids in RNA Interference Therapeutics. ACS Nano 2017, 11, 7572-7586.

Han, X.; Zhang, H.; Butowska, K.; Swingle, K.; Alameh, M.; Weissman, D.; Mitchell, M. An Ionizable Lipid Toolbox for RNA Delivery. Nature Communications 2021, 12, 7233.

Hou, X.; Zaks, T.; Langer, R.; Dong, Y. Lipid Nanoparticles for mRNA Delivery. Nature Reviews Materials 2021, 6, 1078-1094.

Li, S. and Huang, L. Pharmacokinetics and Biodistribution of Nanoparticles. Mol. Pharmaceutics 2008, 5, 4, 496-504.

Incorporation by Reference

For all purposes, each and every publication and patent document cited in this disclosure is hereby incorporated herein by reference in its entirety for all purposes to the same extent as if each such publication or document was specifically and individually indicated to be incorporated herein by reference. This includes the information provided in X. Hou et al., Lipid nanoparticles for mRNA delivery, Nat Rev Materials 2021, 10:1-17, and U.S. Pat. Nos. 9,393,215 and 10,266,485.

Practice of the Invention

The technology provided in this disclosure and its use is described within a hypothetical understanding of general principles of lipid chemistry, nucleic acid chemistry, and the formulation and use of pharmaceutical products. These discussions are provided for the edification and interest of the reader, and are not intended to limit the practice of the claimed invention. The silyl lipids of the disclosure can be used for various purposes, including but not limited to the making lipid nanoparticles. In turn the LNPs of the disclosure can be used for various purposes, including but not limited a role as a delivery vehicle for pharmaceutical agents. All of the products and methods claimed in this application may be used for any suitable purpose without restriction, unless otherwise indicated or required. The silyl lipids and LNPs are believed to be safe, but at the time of this writing, have not been tested for safety or efficacy in human subjects.

While the invention has been described with reference to the specific examples and illustrations, changes can be made and equivalents can be substituted to adapt the technology to a particular context or intended use as a matter of routine development and optimization and within the purview of one of ordinary skill in the art, thereby achieving benefits of the invention without departing from the scope of what is claimed and their equivalents.

The invention claimed is:

1. A silyl lipid having the structure shown in Formula III or Formula IIIa:

[Formula III]

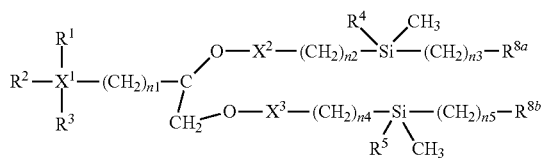

[Formula IIIa]

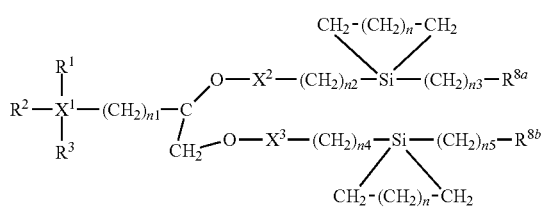

wherein $R^1$, $R^2$, and $R^3$ are independently H, —$CH_3$, or a substituted or unsubstituted hydrocarbon containing two to ten carbon atoms, $X^1$ is nitrogen or —$(OPO_3)$—, $X^2$ and $X^3$ are independently methylene or carbonyl or together are a quaternary carbon;

$R^4$ and $R^5$ are independently selected from methyl and a hydrocarbon or substituted hydrocarbon of 4 to 12 carbon atoms;

$R^{8a}$ and $R^{8b}$ are independently methyl or a saturated or unsaturated hydrocarbon of 2 to 10 carbon atoms;

n1 is 1 to 6; and n2, n3, n4 and n5 are independently 4 to 12.

2. The silyl lipid of claim 1, having the structure shown in Formula IV.

[Formula IV]

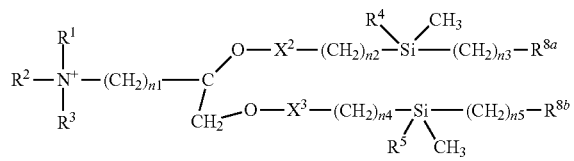

3. The silyl lipid of claim 1, having the structure shown in Formula V.

[Formula V]

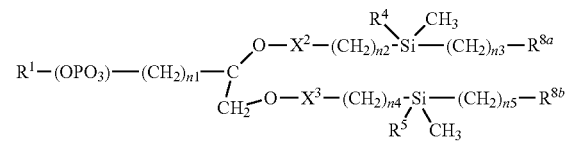

4. The silyl lipid of claim 2, wherein $R^1$, $R^2$, and $R^3$ are all —$CH_3$.

5. The silyl lipid of claim 1, wherein $R^1$ and $R^2$ are both —$CH_3$ and $R^3$ is a linear hydrocarbon containing two to ten carbon atoms, or wherein $R^1$ is H, $R^2$ is —$CH_3$ and $R^3$ is a linear hydrocarbon containing two to ten carbon atoms.

6. The silyl lipid of claim 1, wherein n1 is 1.

7. The silyl lipid of claim 1, wherein $X^2$ and $X^3$ are both methylene or both carbonyl.

8. The silyl lipid of claim 1, wherein n2 and n4 are both 5, and n3 and n5 are both 7.

9. The silyl lipid of claim 1, having the structure shown in Formula III, wherein $R^4$ and $R^5$ are both methyl.

10. The silyl lipid of claim 1, having the structure shown in Formula III, wherein $R^4$ and $R^5$ are both independently a substituted hydrocarbon of 6 to 10 carbon atoms.

11. The silyl lipid of claim 1, wherein $R^{8a}$ and $R^{8b}$ are both methyl.

12. The silyl lipid of claim 1, which is PEGylated, wherein any one or more of $R^1$, $R^2$, and $R^3$ contain —O—$[CH_2—CH_2—O—]_{n9}$—$R^9$, wherein $R^9$ is —OH, —$OCH_3$, —$NH_2$, or a substituted hydrocarbon, and n9 is an integer of 10 or more.

13. The silyl lipid of claim 1, which is one of the following: Silyl-DOTAP, Silyl-DOTMA, Silyl-DOPE, and Silyl-DOPE-PEG.

14. The silyl lipid of claim 3, having the structure shown in Formula VI.

[Formula VI]

$n_1 = 2, 4, 5$
$n_2 = 1, 3, 5, 6, 8$

Silyl-DOPE

15. The silyl lipid of claim 1, contained in a lipid nanoparticle that also contains a drug payload, wherein at least 5% of lipid molecules in the nanoparticles are silyl lipids.

16. The silyl lipid of claim 15, wherein the drug payload comprises a nucleic acid for gene therapy or immunization of a subject in need thereof.

17. The silyl lipid of claim 15, wherein the drug payload includes a protein antigen expressed by severe acute respiratory syndrome coronavirus 2 (SARS-COV-2), or a nucleic acid encoding said protein antigen.

18. A method of using a silyl lipid according to claim 1 to prepare a lipid nanoparticle for pharmaceutical use, the method comprising:
    enveloping a drug payload for treatment of a patient in need thereof in a lipid nanoparticle that is 20 to 200 nm in diameter and contains least 5% of said silyl lipids (wt/wt) in cationic or ionizable form.

* * * * *